United States Patent [19]

Castro Pineiro et al.

[11] Patent Number: 5,681,833
[45] Date of Patent: Oct. 28, 1997

[54] BENZODIAZEPINE DERIVATIVES

[75] Inventors: Jose Luis Castro Pineiro, Harlow; Mark Stuart Chambers, Watford; Sarah Christine Hobbs, Bishops Stortford; Victor Giulio Matassa, Furneux Pelham, all of United Kingdom

[73] Assignee: Merck, Sharp & Dohme Ltd., Hoddesdon, England

[21] Appl. No.: 302,936

[22] PCT Filed: Mar. 23, 1993

[86] PCT No.: PCT/GB93/00599

§ 371 Date: Sep. 20, 1994

§ 102(e) Date: Sep. 20, 1994

[87] PCT Pub. No.: WO93/19052

PCT Pub. Date: Sep. 30, 1993

[30] Foreign Application Priority Data

| Mar. 24, 1992 | [GB] | United Kingdom | 9206317 |
| Mar. 26, 1992 | [GB] | United Kingdom | 9206653 |
| Aug. 28, 1992 | [GB] | United Kingdom | 9218386 |
| Nov. 11, 1992 | [GB] | United Kingdom | 9223582 |

[51] Int. Cl.⁶ .......... A61K 31/55; C07D 403/12; C07D 243/14; C07D 243/24
[52] U.S. Cl. .......... 514/215; 540/504
[58] Field of Search .......... 540/509; 514/215

[56] References Cited

FOREIGN PATENT DOCUMENTS

| 0 167 919 A2 | 1/1986 | European Pat. Off. |
| 0 434 360 A1 | 6/1991 | European Pat. Off. |
| 0 434 364 A3 | 6/1991 | European Pat. Off. |
| 0 434 369 A1 | 6/1991 | European Pat. Off. |
| 0 508 796 A1 | 10/1992 | European Pat. Off. |
| 0 508 797 A1 | 10/1992 | European Pat. Off. |
| 0 508 799 A1 | 10/1992 | European Pat. Off. |
| 514133 | 11/1992 | European Pat. Off. |
| WO92/01683 | 2/1993 | WIPO |

OTHER PUBLICATIONS

J. Med. Chem. 1989, vol. 32, pp. 13–16, Mark G. Bock, et al. entitled "Benzodiazepine Gastrin and Brain Cholecystokinin Receptor Ligands: L–365,260".

Patel, S. et al "Biological Properties of the Benzodiazepine AMidine Derivative L–740,093, a Cholecystokinin–B/Gastrin Receptor Antagonist with High Affinity in Vitro and High Potency In Vivo" Molecular Pharmacology:46 1994 pp. 943–948.

Kawabata, S. et al. "Effect of cholecystokinin receptor antagonists. MK–329 and L–365,260 on cholecystokinin–induced acid secretion and histidine decarboxylase activity in the rat" Regulatory Peptides: 35 1991 pp. 1–10.

Woodruff, Neuropeptides 19, (Suppl) pp. 45–56 (1991).

*Primary Examiner*—Mark L. Berch
*Attorney, Agent, or Firm*—Robert J. North; Melvin Winokur

[57] ABSTRACT

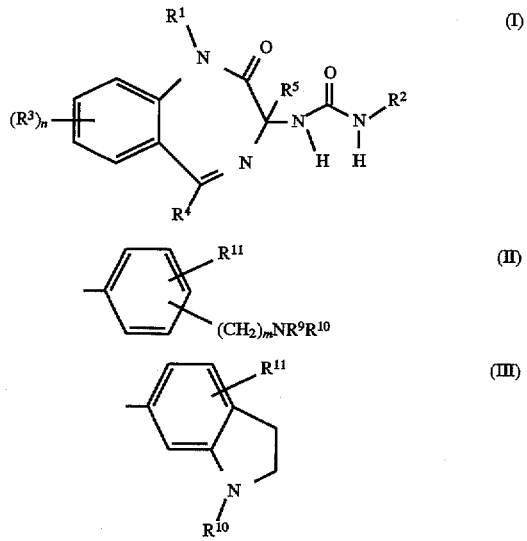

Compounds of Formula (I), and salts and prodrugs thereof, wherein said formula, $R^1$ represents certain optionally substituted alkyl or $C_{3-7}$cycloalkyl; $R^2$ represents (II) or (III), where m is 0, 1, 2 or 3; $R^9$ is H or $C_{1-6}$alkyl; $R^{10}$ is imidazolyl, triazolyl or tetrazolyl, and $R^{11}$ is H, $C_{1-6}$alkyl or halo; $R^3$ is $C_{1-6}$alkyl, halo or $NR^6R^7$; $R^4$ is $C_{1-7}$alkyl, $C_{3-10}$cycloalkyl, $C_{3-10}$cycloalkyl$C_{1-4}$alkyl, $C_{6-10}$bicycloalkyl, optionally substituted aryl, or $NR_{12}R_{13}$; $R^5$ is H or $C_{1-4}$alkyl; n is 0, 1, 2 or 3; which are CCK and/or gastrin antagonists useful in therapy.

11 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

Trp Met Asp Phe
1

BENZODIAZEPINE DERIVATIVES

This application is a 35 U.S.C. § 371 application of PCT/GB93/00599, filed Mar. 23, 1993.

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p. 169 and G. Nission, ibid. p. 127).

Cholecystokinins include CCK-33, a neuropeptide. Of thirty-three amino acids in its originally isolated form (see, Mutt and Jorpes, *Biochem. J.* 125, 678 (1971)), its carboxy-lterminal octapeptide, CCK-8 (also a naturally-occurring neuropeptide and the minimum fully active sequence), and 39- and 12-amino acid forms. Gastrin occurs in 34-, 17- and 14-amino acid forms, with he minimum active sequence being the C-terminal tetrapeptide, Trp-Met-Asp-Phe-$NH_2$, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et el., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et at., "Two brain cholecystokinin receptors: implications for behavioural actions", *Brain Res.*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M.F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta *Physiol. Scand.*, 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

European patent application no. 0 167 919 discloses benzodiazepine CCK and gastrin receptor antagonists substituted at the 3-position by inter alia, a phenyl urea, and at the 5-position by a phenyl or $C_{1-4}$alkyl group. There is no disclosure of the phenyl urea substitution of the compounds of the present invention.

The present invention provides benzodiazepine compounds of formula (I)

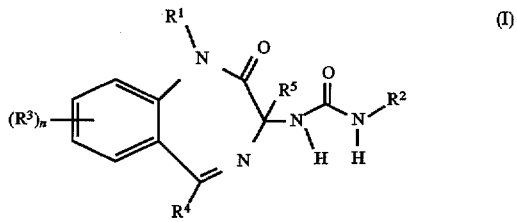

wherein:

$R^1$ represents $(CH_2)_q$imidazolyl, $(CH_2)_q$tetrazolyl, $(CH_2)_q$triazolyl, (where q is 1, 2 or 3); $C_{1-6}$alkyl optionally substituted by one or more groups selected from halo, hydroxy and $NR^6R^7$ (where $R^6$ and $R^7$ each independently represents H or $C_{1-4}$alkyl, or $R^6$ and $R^7$ together form a chain $(CH_2)_p$ where p is 4 or 5); $C_{3-7}$cycloalkyl; cyclopropylmethyl; $CH_2CO_2R^8$ (where $R^8$ is $C_{1-4}$alkyl); $CH_2CONR^6R^7$; or $CH_2CH(OH)$—W—$(CH_2)_2NR^6R^7$ where W is S or NH and $R^6$ and $R^7$ are as previously defined;

$R^2$ represents

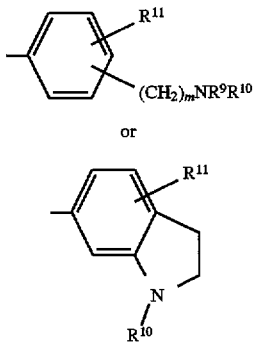

where m is 0, 1, 2 or 3; $R^9$ represents H or $C_{1-6}$alkyl; $R^{10}$ represents imidazolyl, triazolyl or tetrazolyl, any of which may be optionally substituted by $C_{1-4}$alkyl; and $R^{11}$ represents H, $C_{1-6}$alkyl or halo;

$R^3$ represents $C_{1-6}$alkyl, halo or $NR^6R^7$, where $R^6$ and $R^7$ are as previously defined;

$R_4$ represents $C_{1-7}$alkyl, $C_{3-10}$cycloalkyl optionally substituted by one or more $C_{1-4}$alkyl groups, $C_{3-10}$cycloalkyl$C_{1-4}$alkyl, $C_{6-10}$-bicycloalkyl, aryl optionally substituted by one or more substituents selected from ($C_{1-4}$alkyl, $C_{1-4}$alkoxy, hydroxy, halo and trifluoromethyl) or $NR^{12}R^{13}$ where $R^{12}$ and $R^{13}$ each independently represent H, $C_{1-12}$alkyl, $C_{3-10}$cycloalkyl optionally substituted by one or more $C_{1-4}$alkyl groups, $C_{3-10}$cycloalkyl$C_{1-4}$alkyl, optionally substituted aryl, optionally substituted aryl$C_{1-6}$alkyl or azacyclic or azabicyclic groups, or $R^{12}$ and $R^{13}$ together form the residue of an optionally substituted azacyclic or azabicyclic ring system;

$R^5$ represents H or $C_{1-4}$alkyl;

n is 0, 1, 2 or 3; and salts and prodrugs thereof.

As used herein, the definition of each expression, when it occurs more than once in any structure, is intended to be independent of its definition elsewhere in the same structure.

It will be appreciated that formula (I) is intended to embrace all possible isomers, including optical isomers, and mixtures thereof, including racemates.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

As used herein, alkyl means linear or branched saturated hydrocarbon. Examples of suitable alkyl groups include methyl, ethyl, propyl, isopropyl and isobutyl groups.

When $R^1$ represents cycloalkyl, examples of suitable cycloalkyl groups include cyclopropyl, cyclopentyl and cyclohexyl groups, preferably cyclopropyl.

Halo includes fluoro, chloro, bromo and iodo.

When $R^4$ represents $C_{1-7}$alkyl, suitable alkyl groups include methyl, ethyl, isopropyl and t-butyl.

When $R^4$ represents $C_{3-10}$cycloalkyl optionally substituted by one or more $C_{1-4}$alkyl groups, it will suitably represent optionally substituted cyclobutyl, cyclopentyl, cyclohexyl or cycloheptyl, preferably cyclohexyl or cycloheptyl optionally substituted by one or more $C_{1-4}$alkyl, preferably methyl, groups.

When $R^4$ represents $C_{6-10}$bicycloalkyl, it will preferably contain 7, 8 or 9 carbon atoms, more preferably 7 carbon atoms. A suitable example of a $C_{6-10}$bicycloalkyl substituent is [2.2.1]bicycloheptanyl.

When $R^4$ is aryl this may be a 5- or 6-membered ring system, optionally containing one or more heteroatoms, for example, pyridyl, thienyl or phenyl.

When $R^4$ is $NR^{12}R^{13}$ and $R^{12}$ or $R^{13}$ represents optionally substituted aryl or optionally substituted aryl$C_{1-6}$alkyl, suitable aryl groups include phenyl, thienyl, furyl, pyrrolyl and pyridinyl, preferably phenyl. Suitable aryl substituents include, for example, $C_{1-4}$alkyl, $C_{1-4}$alkoxy, halo and trifluoromethyl.

When $R^{12}$ or $R^{13}$ represents an azacyclic or azabicyclic group, the azacyclic or azabicyclic group may contain, in addition to the nitrogen atom, a further heteroatom selected from O and S, or a group $NR^{15}$, where $R^{15}$ is H or $C_{1-4}$alkyl.

When $R^{12}$ or $R^{13}$ represents an azacyclic group, it will suitably contain from 5 to 10 ring atoms.

When $R^{12}$ or $R^{13}$ represents an azabicyclic group, it will suitably contain from 7 to 10 ring atoms.

When $R^{12}$ and $R^{13}$ together form the residue of an azacyclic ring, the substituent —$NR^{12}R^{13}$ may be represented as

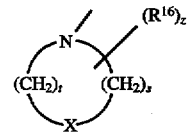

wherein

X represents O, S, $NR^{17}$ or $CH_2$ where $R^{17}$ represents H, $C_{1-4}$alkyl, $CO_2R^a$, $COR^a$ or $SO_2R^a$ where $R^a$ is $C_{1-6}$alkyl, optionally substituted phenyl or benzyl optionally substituted in the phenyl ring by one or more substituents, where the phenyl substituents are selected from $C_{1-4}$alkyl, $C_{1-4}$alkoxy, halo and trifluoromethyl;

$R^{16}$ is $C_{1-6}$alkyl, $C_{1-6}$alkoxy, hydroxy, oxo, $SC_{1-4}$alkyl, $NR^6R^7$, $NR_9C_{1-4}$alkyl$R^{18}$, =$NOR^9$, or

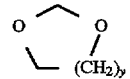

where $R^6$, $R^7$ and $R^9$ are as previously defined, $R^{18}$ is halo or trifluoromethyl and y is 2 or 3;

s is 2, 3 or 4;

t is 1, 2, 3, 4, 5, 6, 7 or 8 when X is $CH_2$, or 2, 3, 4, 5, 6, 7 or 8 when X is O, S or $NR^{17}$;

z is 0, 1, 2, 3, 4, 5, 6, 7 or 8; and each $R^{16}$ may be located on any available carbon atom of the azacyclic ring system. In particular, geminal disubstitution on one or more carbon atoms of the azacyclic ring is provided for.

Preferably X represents O, N—H, N—$CH_3$ or $CH_2$.

Preferably s is 2.

When X is O, S or $NR^4$, t is preferably 2 or 3. When X is $CH_2$, t is preferably 2, 3, 4 or 5.

When $R^{12}$ and $R^{13}$ together form the residue of a bridged azabicyclic ring system, the ring system $NR^{12}R^{13}$ will be non-aromatic and may contain, in addition to the nitrogen atom to which $R^{12}$ and $R^{13}$ are attached, a second heteroatom selected from O and S, or a group $NR^{17}$, where $R^{17}$ is as previously defined. Suitably the azabicyclic ring system contains from 7 to 10 ring atoms, preferably 7, 8 or 9 ring atoms. The azabicyclic ring system may be bridged, or the two rings may be fused either through a bond or through an atom. Where the rings are fused through an atom the resulting azabicyclic ring system may be referred to as a spiro azabicyclic ring system.

Preferably $R^1$ is $C_{1-6}$alkyl, such as methyl, n-propyl, isobutyl or t-butyl, more preferably methyl.

Preferably $R^2$ represents

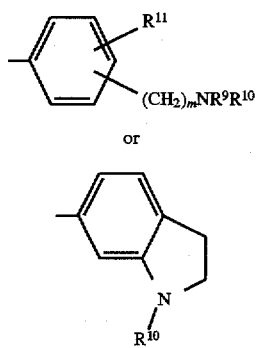

Wherein $R^9$ preferably represents H or methyl; $R^{10}$ suitably represents tetrazolyl such as tetrazol-5-yl or imidazolyl such as imidazol-2-yl, preferably tetrazol-5-yl; $R^{11}$ preferably represents H or methyl; and m is preferably 0 or 1.

Suitable values for $R^3$ include methyl, dimethylamino, chloro and bromo.

Preferably n is 0 or 1, more preferably 0.

Preferred values for $R^4$ include $C_{3-10}$cycloalkyl, such as $C_{3-7}$cycloalkyl, for example cyclobutyl, cyclopentyl, cyclohexyl and cycloheptyl; aryl, such as phenyl; and $NR^{12}R^{13}$, such as

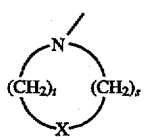

wherein s, t and X are as previously defined, s and t preferably each represent 2 and X preferably represents $NR^{17}$, especially $NCH_3$.

A further apt value for $R^4$ is azabicyclo, especially [3.2.2] nonan-3-yl.

In one preferred group of compounds according to the invention, $R^5$ represents H.

In a further preferred group of compounds according to the invention, $R^5$ represents methyl.

A subgroup of compounds according to the invention is represented by compounds of formula (I) wherein $R^{10}$ represents tetrazolyl optionally substituted by $C_{1-4}$alkyl; $R^3$ represents $C_{1-6}$alkyl or halo; $R^4$ represents $C_{1-7}$alkyl, $C_{3-7}$cycloalkyl, $C_{4-7}$cycloalkylalkyl or aryl optionally substituted by one or more substituents selected from $C_{1-4}$alkyl, $C_{1-4}$alkoxy, hydroxy, halo and trifluoromethyl; m is 0, 1 or 2; and n is 0, 1 or 2.

Within this subgroup is a further subclass of compounds wherein $R^2$ is

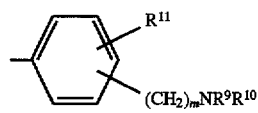

and $R^5$ is H.

A further subgroup of compounds according to the invention is represented by compounds of formula (I) wherein $R^1$ represents $C_{1-6}$alkyl, $C_{3-7}$cycloalkyl, cyclopropylmethyl, $CH_2CO_2R^8$ or $CH_2CONR^6R^7$ (where $R^6$, $R^7$ and $R^8$ are as previously defined); $R^2$ is

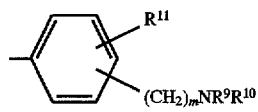

wherein $R^9$, $R^{11}$ and m are as defined for formula (I) and $R^{10}$ represents an imidazolyl group, optionally substituted by $C_{1-4}$alkyl; $R^4$ represents bridged $C_{6-10}$bicycloalkyl or $C_{3-7}$cycloalkyl optionally substituted by one or more $C_{1-4}$alkyl groups; and $R^5$ is H.

A preferred subgroup of compounds according to the invention is represented by compounds of formula (IA), and salts and prodrugs thereof:

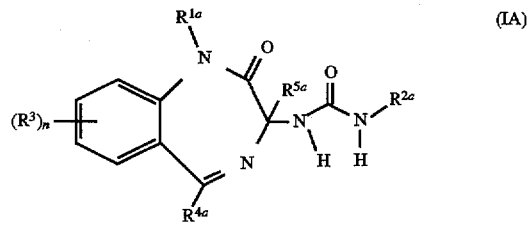

(IA)

wherein $R^{1a}$ represents $C_{1-6}$alkyl, preferably $C_{1-4}$alkyl; $R^{2a}$ represents

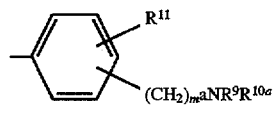

or

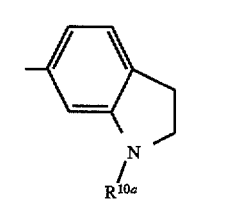

wherein $R^9$ is as defined for formula (I), preferably H or methyl; $R^{10a}$ is tetrazolyl or imidazolyl, preferably tetrazolyl; $R^{11}$ is as defined for formula (I), preferably H or methyl; and $m^a$ is 0 or 1;

$R^3$ is as defined for formula (I), preferably methyl, dimethylamino, chloro or bromo;

$R^{4a}$ is $C_{3-10}$cycloalkyl, preferably $C_{4-7}$cycloalkyl, aryl, preferably phenyl, or $NR^{12}R^{13}$ where $R^{12}$ and $R^{13}$ are as previously defined and preferably form the residue of an azacycle;

$R^{5a}$ is H or methyl, preferably H; and n is as defined for formula (I), preferably 0.

Preferably the salts of the compounds of formula (I) are pharmaceutically acceptable, but non-pharmaceutically acceptable salts may be used for the preparation of pharmaceutically acceptable salts.

The present invention provides compounds of formula (I) and their pharmaceutically accepatable salts.

The pharmaceutically acceptable salts of the compounds of formula (I) include the conventional salts or the quaternary ammonium salts of the compounds of formula (I) formed, e.g., from non-toxic inorganic or organic acids or bases. For example, such conventional non-toxic salts include basic salts, e.g. sodium and potassium salts and those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The pharmaceutically acceptable salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or combination of solvents.

For example, an acidic compound of formula (I) may be reacted with an appropriate amount of a base, such as an alkali or alkaline earth metal hydroxide e.g. sodium, potassium, lithium, calcium, or magnesium, or an organic base such as an amine, e.g. dibenzylethylenediamine, trimethylamine, piperidine, pyrrolidine, benzylamine, and the like, or a quaternary ammonium hydroxide such as tetramethylammonium hydroxide.

The compounds of formula (I) and their salts and prodrugs, may be administered to animals, preferably to mammals, and most especially to a human subject either alone or, preferably, in combination with pharmaceutically acceptable carriers, optionally with known adjuvants, such as alum, in a pharmaceutical compostion, according to standard pharmaceutical practice. The compounds can be administered orally, parenterally, including by intravenous, intramuscular, intraperitoneal or subcutaneous administration, or topically.

The present invention thus provides a pharmaceutical composition comprising a compound of formula (I), or a salt or prodrug thereof, and a pharmaceutically acceptable carrier therefor.

The present invention also provides a process for the preparation of a pharmaceutical composition comprising a compound of formula (I) or a salt or prodrug thereof, which process comprises bringing a compound of formula (I), or a salt or prodrug thereof, into association with a pharmaceutically acceptably carrier.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage will be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by intravenous administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared by processes analogous to those described in European Patent Specification No. 0284256. For example, a compound of formula (I) may be prepared by reaction of an intermediate of formula (II) with a compound of formula (III)

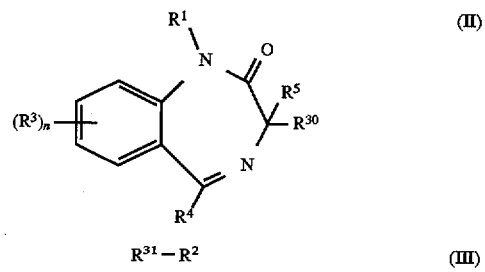

$R^{31}-R^2$ (III)

wherein $R^1$, $R^2$, $R^3$, $R^4$, $R^5$ and n are as defined for formula (I), one of $R^{30}$ and $R^{31}$ represents $NH_2$ and the other of $R^{30}$ and $R^{31}$ represents N=C=O or an activated carbamate.

When one of $R^{30}$ and $R^{31}$ represents N=C=O, the reaction is preferably conducted in a suitable organic solvent, such as an ether, for example, tetrahydrofuran, at room temperature.

When one of $R^{30}$ and $R^{31}$ represents an activated carbamate the reaction is effected in the presence of a base. Suitable bases for use in the reaction include tertiary amines, for example, triethylamine. Preferably $R^{30}$ represents an activated carbamate and $R^{31}$ represents $NH_2$.

The activated carbamate will suitably be an appropriately substituted aryl carbamate, for example

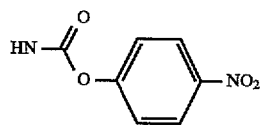

The reaction is conveniently effected in a suitable organic solvent, for example, dimethylformamide, at ambient or elevated temperature. Preferably the reaction is conducted at approximately 50° C.

Intermediates of formula (II) wherein $R^{30}$ is N=C=O (hereinafter intermediates (IIB)) may be prepared from corresponding amines of formula (II) wherein $R^{30}$ is $NH_2$ (hereinafter intermediates (IIA)) by conventional methods, for example, by treatment with triphosgene.

Intermediates of formula (II) where $R^{30}$ is an activated carbamate (hereinafter intermediates (IIC)) may be prepared from compounds of formula (IIA) by reaction with a suitable chloroformate, for example

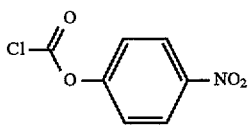

in the presence of a base, such as a tertiary amine, for example, triethylamine.

Intermediates of formula (IIA) wherein $R^5$ is H may be prepared from compounds of formula (VI)

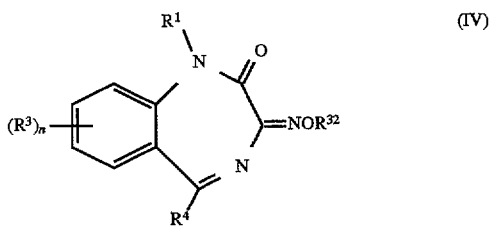

wherein $R^1$, $R^3$, $R^4$ and n are as defined for formula (I) above, and $R^{32}$ represents H or a group C(=O)NHalkyl, by reduction, for example, by catalytic hydrogenation or reduction using a suitable metal under acidic conditions.

Suitable hydrogenation catalysts include, for example, nobel metal catalysts, e.g. ruthenium, or rhodium which may be supported, for example, on carbon.

The reaction is preferably conducted in a suitable organic solvent, such as an alcohol, for example, methanol, at elevated temperature, e.g. about 60° C.

Suitable reduction methods using metals include, for example, the use of zinc and trifluoroacetic acid in a suitable solvent, such as acetic acid, preferably at elevated temperature, e.g. at about 40° C.

Alternatively, intermediates of formula (IIA) may be prepared from compounds of formula (V)

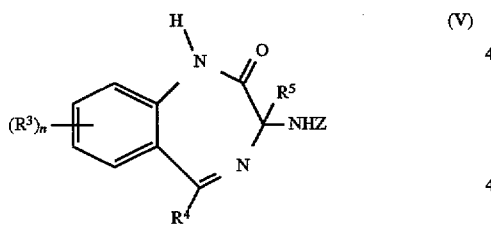

wherein $R^3$, $R^4$, $R^5$ and n are as defined for formula (I) and Z is a protecting group; by reaction with a reagent suitable to introduce the group $R^1$, for example a halide of formula $R^1$Hal where Hal represents halo such as bromo or iodo, in the presence of a base, such as an alkali metal hydride or an alkaline earth metal carbonate, for example sodium hydride or caesium carbonate; or a suitable dialkyl acetal of dimethyl formamide in a suitable organic solvent, e.g. toluene followed by deprotection.

Compounds of formula (IIA) wherein $R^5$ is $C_{1-4}$alkyl may also be prepared from the corresponding compounds of formula (IIA) wherein $R^5$ is H by a reaction sequence comprising the following steps:

(i) Reaction with a suitable aldehyde, such as benzaldehyde, in the presence of a dehydrating agent, such as anhydrous magnesium sulphate or 4 Å molecular sieves, preferably in a suitable anhydrous organic solvent, such as anhydrous dichloromethane.

(ii) Treatment with an alkali metal bis(trimethylsilyl) amide, such as sodium bis(trimethylsilyl)amide, preferably in a suitable organic solvent, such as an ether, for example, tetrahydrofuran, at low temperature, such as at about −70° C.

(iii) Alkylation using a reagent suitable to introduce the group $R^5$, such as an alkyl halide of formula $R^5$-Hal, where $R^5$ is $C_{1-4}$alkyl and Hal is bromo, chloro or iodo, preferably iodo.

Intermediates of formula (IV) wherein $R^{32}$ is C(=O) NHalkyl. (hereinafter intermediates (IVB)) may be prepared from intermediates of formula (IV) wherein $R^{32}$ is H (hereinafter intermediates (IRA)) by reaction with an alkylisocyanate. The reaction is conveniently effected in a suitable organic solvent, such as an ether, for example, tetrahydrofuran, suitably at elevated temperature, such as about 60°.

Intermediates of formula (IVA) may be prepared from compounds of formula (VI)

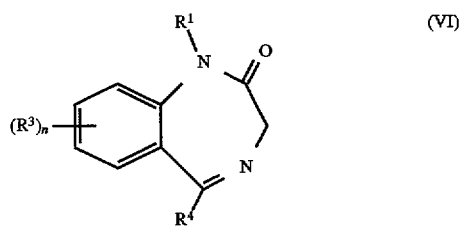

wherein $R^1$, $R^3$, $R^4$ and n are as defined for formula (I), by reaction with isoamyl nitrite in the presence of a base.

Suitable bases of use in the reaction include alkali metal alkoxides, such as potassium-t-butoxide.

Compounds of formula (VI) wherein $R^4$ represents $NR^{12}R^{13}$ may be prepared from compounds of formula (VII)

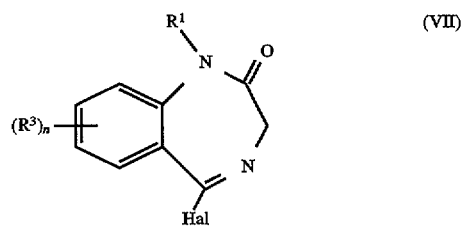

wherein $R^1$, $R^3$ and n are as defined for formula (I) and Hal represents halo, such as chloro, by reaction with an amine of formula $HNR^{12}R^{13}$, wherein $R^{12}$ and $R^{13}$ are as defined for formula (I).

The preparation of compounds of formula (VII) is described in United Kingdom Patent Specification No. 1,145,471.

Compounds of formula (V) wherein $R^4$ is other than $NR^{12}R^{13}$ may be prepared from compounds of formula (VIII)

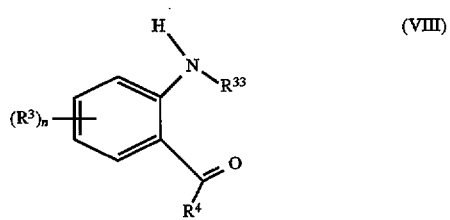

wherein $R^3$, $R^4$ and n are is as defined for formula (I) and $R^{33}$ is H, by a reaction sequence comprising:

(i) reaction with a compound of formula (IX)

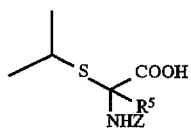

wherein $R^5$ and Z are as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC), isobutyl chloroformate or, preferably, bis(2-oxo-3-oxazolidinyl) phosphonic chloride (BOP-Cl);

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran;

(iii) Treatment with an organic acid, for example acetic or propionic acid, optionally in the presence of an ammonium salt, for example ammonium acetate.

The preparation of compounds of formula (VIII) is described in European Patent Application no. 0514133.

Intermediates of formula (III) wherein $R^{31}$ is N=C=O or an activated carbamate may be prepared from compounds of formula (III) wherein $R^{31}$ is $NH_2$ (hereinafter intermediates (IIIA)) by procedures analogous to those described for the preparation of compounds of formula (IIB) and (IIC).

Amines of formula (IIIA) may be prepared from the corresponding nitro compounds of formula $R^2NO_2$ wherein $R^2$ is as defined for formula (I), by reduction.

Suitably the reduction is effected by catalytic hydrogenation, for example, using a noble metal catalyst such as palladium which may be supported, e.g. on carbon. The reaction is conveniently effected in a suitable organic solvent, such as an alcohol, e.g. methanol.

Compounds of formula $R^2NO_2$ may be prepared by conventional methods. For example, compounds of formula $R^2NO_2$ wherein $R^2$ is phenyl substituted by $(CH_2)_mNR^9R^{10}$ and m is 1 or 2 may be prepared by reaction of a compound of formula (X)

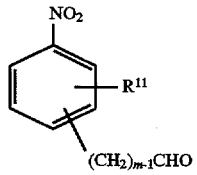

wherein $R^{11}$ and m are as previously defined, with an amine of formula $R^9R^{10}NH$, wherein $R^9$ and $R^{10}$ are as defined for formula (I), in the presence of a reducing agent.

Suitable reducing agents of use in the reaction include hydride reducing agents such as, for example, sodium borohydride. The reaction is conveniently effected in a suitable organic solvent, such as an alcohol, for example, ethanol, suitably at ambient temperature.

Compounds of formula $R^2NO_2$ may alternatively be prepared from the corresponding compounds wherein $NR^9R^{10}$ is replaced by $NH_2$ via a conventional ring-forming sequence, for example, as described by T. Jen et al., *J. Med. Chem.*, 18(1), 90–99 (1975).

Compounds of formula $R^2NO_2$ wherein $R^{10}$ is tetrazolyl may also be prepared by treatment of the corresponding compound wherein $R^{10}$ is replaced by CN with an alkali metal azide, for example, sodium azide, in the presence of an ammonium halide, for example, ammonium chloride. The intermediates may be prepared by reaction of the corresponding nitro compound wherein $R^{10}$ is replaced by H with a cyanogen halide, for example, cyanogen bromide, in the presence of a base, suitably an alkali metal hydroxide, such as, for example, sodium hydroxide, conveniently in an aqueous organic solvent, suitably at low temperature, such as, for example, about 10° C.

The reaction is conveniently effected in a suitable organic solvent, such as an amide, for example, dimethylformamide, preferably at elevated temperature, for example at about 165° C.

Other procedures for the preparation of compounds of formula $R^2NO_2$ will be readily apparent to those skilled in the art, or are described in the accompanying examples.

Intermediates of formula (X) are commercially available or may be prepared from commercially available compounds by conventional techniques well-known to those skilled in the art.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

Enantiospecific synthesis of compounds of formula (I) may be achieved, for example, by reaction of chiral intermediates of formula (II), which chiral intermediates may be prepared from the corresponding racemate by conventional procedures, for example, as described in *J. Org. Chem.*, 52, 955 and 3232, (1987), with compounds of formula (III).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

INTERMEDIATE 1

3(R,S,)-Amino-5-cyclohexyl-1,3-dihydro-1-methyl-2H-1,4-benzodiazepin-2-one 1. (2-Aminophenyl) cyclohexyl methanone
Method A To a cooled (0° C.) and stirred solution of 2-aminobenzonitrile (59.5g) in anhydrous diethyl ether (210 ml) was added dropwise cyclohexylmagnesium chloride (2M in diethyl ether; 700 ml) at such a rate as to maintain the temperature below 25° C. After further 18 hours of stirring at room temperature, the mixture was cooled to −60° C. and treated dropwise (CAUTION! highly exothermic reaction) with 5N hydrochloric acid (600 ml). The mixture was then allowed to warm to room temperature, diluted with additional 5N hydrochloric acid (500 ml) and the ethereal layer was separated. The acidic aqueous solution was basified to pH 4–5 with solid potassium hydroxide and then extracted with ethyl acetate (3×700 ml). The ethereal and ethyl acetate solutions were combined, washed with brine (1) dried (MgSO$_4$) and concentrated under vacuum to give 97 g (94%) of the title compound as a solid, mp 73°–75° C. (cyclohexane); δ$_H$ (360 MHz, CDCl$_3$) 7.76 (1H, dd, J=7.0 and 1.0 Hz), 7.25 (1H, dt, J=6.0 and 1.0 Hz), 6.64 (2H, m), 6.29 (2H, br s), 3.27 (1H, m), 2.09–1.23 (10H, m).

Method B a) (2-Acetamidophenyl) cyclohexyl methanone

Cyclohexylmagnesium bromide (240 ml of a 2M solution in ether (200 ml ) was added dropwise to a solution of 2-methyl-4H-3,1-benzoxazin-4-one (100 g) in ether (1100 ml) at −10° C. over 2 h. The mixture was stirred at this temperature for 2 h, then at ambient temperature for 30 min. After cooling to −10° C. the suspension was treated with 2M HCl (600 ml), keeping the temperature below 0° C. After stirring for 15 min the layers were separated, and the ethereal layer washed sequentially with water (500 ml), 5% sodium hydroxide solution (2×500 ml) and finally water (2×500 ml). The organic layer was separated, dried (MgSO$_4$), evaporated in vacuo and chromatographed on silica using petrol:ethyl acetate (2:1) to give (2-acetamidophenyl) cyclohexyl methanone (28 g) as a solid, mp 66° C.; δ$_H$(CDCl$_3$, 360 MHz) 1.25–1.89 (10H, m), 2.23 (3H, s), 3.33 (1H, m), 7.13 (1H, dt, J=6 and 1 Hz), 7.53 (1H, dt, J=6 and 1 Hz), 7.92 (1H, d, J=6 Hz), 8.76 (1H, d, J=6 Hz), 11.73 (1H, br s).

b) (2-Aminophenyl) cyclohexyl methanone

A solution of (2-acetamidophenyl) cyclohexyl methanone (0.53 g) in methanol (5 ml) and concentrated hydrochloric acid (15 ml) was heated at 80° C. for 1 hour. After this time the solution was cooled to ambient temperature and the solvents removed in vacuo. The residue was dissolved in water (10 ml) and basified with 4N sodium hydroxide solution (20 ml). The mixture was then extracted into ethyl acetate (4×20 ml) and the organic layers combined and dried (MgSO$_4$). The solvent was evaporated and the residue chromatographed on silica gel using petrol:ethyl acetate (2:1), to afford the title compound (0.40 g) as a solid. The spectroscopic properties of this material were identical to those described in Method A.

2. 3(R,S)-[(Benzyloxycarbonyl)amino]-5-cyclohexyl-1,3-dihydro-2H-1,4-benzodiazepin-2-one a-(Isopropylthio)-N-(benzyloxycarbonyl)glycine (30 g,) was dissolved in dichloromethane (1000 ml) and cooled to 0° C. The stirred solution was treated with N-methyl morpholine (11.5 ml) followed by isobutyl chlorformate (13.7 ml). The reaction mixture was stirred for a further 15 min at 0° C., then heated to reflux. The refluxing reaction mixture was treated dropwise, over 20 min, with a solution of (2-aminophenyl) cyclohexyl methanone (20.5 g) in dichloromethane (140 ml). After addition was complete the reaction was heated at reflux for a further 4 h. The mixture was then washed in succession with 10% citric acid solution (2×500 ml), saturated sodium bicarbonate solution (2×500 ml) and brine (500 ml). The dried (MgSO$_4$) organic phase was evaporated to afford the crude product as a solid, which was used without further purification.

The crude (isopropylthio)glycinamide was dissolved in anhydrous tetrahydrofuran (800 ml) and cooled to 0° C. Ammonia gas was bubbled through the stirred solution for 30 min before adding mercuric chloride (33 g) in one portion. Ammonia was continually bubbled through the solution for a further 5 hours, then the suspended solids were filtered off. The solvent was evaporated in vacuo to leave an oil, which was used without further purification.

The crude α-aminoglycinamide was dissolved in glacial acetic acid (500 ml) and treated with ammonium acetate (36.2 g). The resulting reaction mixture was stirred at room temperature overnight, before removing the solvent in vacuo. The residue was partitioned between ethyl acetate (300 ml) and 1N sodium hydroxide solution (300 ml). The organic phase was separated, dried (MgSO$_4$) and evaporated. The residue was chromatographed on silica, using petrol:ethyl acetate (2:1) as the eluent, to afford 3(R,S)-[(benzyloxycarbonyl)amino]-5-cyclohexyl-1,3-dihydro-2H-1,4-benzodiazepin-2-one (25 g as a solid; mp 164°–166° C.; δ$_H$ (360 MHz, CDCl$_3$) 1.07–2.04 (10H, m), 2.77 (1H, m), 5.12 (3H, m) 6.44 (1H, d, J=8 Hz), 7.08 (1H, d, J=8 Hz), 7.23–7.36 (6H, m), 7.46 (1H, t, J=7 Hz), 7.59 (1H, d, J=8 Hz), 8.60 (1H, br s).

3. 3(R,S)-[(Benzyloxycarbonyl)amino]-5-cyclohexyl-1,3-dihydro-1-methyl-2H-1,4-benzodiazepin-2-one To a refluxing solution of 3(R,S)-[(benzyloxycarbonyl)amino]-5-cyclohexyl-1,3-dihydro-2H-1,4-benzodiazepin-2-one (5 g) in anhydrous toluene (400 ml) was added dimethylformamide dimethylacetal (7.3 ml) and the mixture was refluxed for 3.5 hours under nitrogen before additional dimethylformamide dimethyl acetal (1 ml) was added. After a further 50 minutes at reflux, solvents were removed under vacuum and the residue was triturated with diethyl ether (50 ml). The white solid was collected by filtration, washed with diethyl ether (2×20 ml) and dried to give the title compound (5 g); mp 205°–207° C.; d$_H$ (360 MHz, CDCl$_3$) 7.55–7.25 (9H, m), 6.52 (1H, d, J=8.0 Hz), 5.10 (3H, m), 3.36 (3H, s), 2.76 (1H, m), 2.04–1.03 (10H, m).

4. 3(R,S)-Amino-5-cyclohexyl-1,3-dihydro-1-methyl-2H-1,4-benzodiazepin-2-one

A mixture of 3(R,S)-[(benzyloxycarbonyl)amino]-5-cyclohexyl-1,3-dihydro-1-methyl-2H-1,4-benzodiazepin-2-one (3.0 g) and hydrobromic acid (45% in acetic acid; 6.2 ml) was stirred for 1 hour at room temperature under a nitrogen atmosphere. The mixture was then diluted with cold anhydrous diethyl ether (40 ml) and it was stirred at 0° C. for 45 minutes. The white precipitate was collected by filtration, washed with cold diethyl ether (4×30 ml) and then dissolved in a mixture of water (30 ml) and 2N sodium hydroxide (15 ml). The basic aqueous phase was extracted with ethyl acetate (3×70 ml) and the combined organic solutions were washed with brine (1×30 ml), dried (Na$_2$SO$_4$) and concentrated. Flash chromatography of the remaining pale red oil (silica gel, dichloromethane-methanol, 94:6) gave the title compound (1.6 g) as a waxy solid; δ$_H$ (250 MHz, CDCl$_3$) 7.53–7.45 (2H, m), 7.28–7.20 (2H, m), 4.30 (1H, s), 3.39 (3H, s), 2.75 (1H, m), 2.04–1.03 (10H, m); m/z (CI) 272 (M$^+$+1).

INTERMEDIATE 2

5-Cyclohexyl-1,3-dihydro-1-methyl-3(R,S)-[(4-nitrophenyloxycarbonyl)amino]-2H-1,4-benzodiazepin-2-one To a cooled (0° C.) and stirred solution of Intermediate 1 (1 g) in anhydrous tetrahydrofuran (20 ml) was added anhydrous triethylamine (0.51 ml) followed by a solution of 4-nitrophenyl chloroformate (0.75 g) in anhydrous tetrahydrofuran (10 ml) over 10 minutes, under nitrogen. The mixture was allowed to warm to room temperature and stirred for further 20 minutes before a white precipitate was removed by filtration and the solvent was evaporated under vacuum. The remaining solid was triturated with anhydrous diethyl ether to give the title compound (1.2 g) as a white solid; mp 165°–168° C.; $\delta_H$ (360 MHz, CDCl$_3$) 8.23 (2H, d, J=7.1 Hz), 7.57 (2H, m), 7.30 (4H, m), 6.90 (1H, d, J=8.2 Hz), 5.18 (1H, d, J=8.2 Hz), 3.43 (3H, s),2.80 (1H, m), 2.05 (1H, m), 1.87 (1H, m), 1.65 (3H, m), 1.55 (1H, m), 1.42–1.18 (3H, m), 1.05 (1H, m).

INTERMEDIATE 3

(+)-3(R)-Amino-5-cyclohexyl-1,3-dihydro-1-methyl-2H-1,4-benzodiazepin-2-one 1. 3(R,S)-[2(R)-(tert-Butyloxycarbonyl)amino-3-phenylpropionyl]amino-5-cyclohexyl-1,3-dihydro-1-methyl-2H-1,4 benzodiazepin-2-one To a solution of Intermediate 1 (4.0 g) in anhydrous dimethylformamide (35 ml) were added in succession BOC-D-phenylalanine (4.11 g), 1-hydroxy-benzotriazole trihydrate (2.09 g) and 1-ethyl-3-[3-(dimethylamino)propyl] carbodiimide hydrochloride (2.97 g), under a nitrogen atmosphere. Anhydrous triethylamine (2.16 ml) was then added and the resulting suspension was stirred at ambient temperature for 20 minutes. The solvent was removed under vacuum, 10% aqueous citric acid (50 ml) was added to the remaining residue and products were extracted with ethyl acetate (4×50 ml). The combined organic phases were washed with 10% aqueous sodium hydroxide (50 ml), water (50 ml) and brine (50 ml), dried (MgSO$_4$) and concentrated. Flash chromatography of the residue (silica gel, petroleum ether-ethyl acetate, 50:50) gave of the title compound (7.26 g) as a solid; mp 95°–98° C.; $d_H$ (360 MHz, CDCl$_3$) 7.58–7.49 (2H, m), 7.32–7.19 (7H, m), 5.34–5.28 (2H, m), 4.98 (1H, br s), 4.53 (1H, br s), 3.38 (3H, s), 3.24–3.10 (2H, m), 2.83–2.73 (1H, m), 2.06–1.98 (1H, m), 1.92–1.83 (1H, m), 1.40 (9H, s), 1.72–1.16 (7H, m), 1.11–0.99 (1H, m); m/z (CI) 518 (M⁻).

2. (+)-3(R)-[2(R)-Amino-3-phenylpropionyl]amino-5-cyclohexyl-1,3-dihydro-1-methyl-2H-1,4-benzodiazepin-2-one Hydrogen chloride gas was bubbled through a cooled (0° C.) solution of 3(R,S)-[2(R)-(tert-butyloxycarbonyl)amino-3-phenyl propionyl]amino-5-cyclohexyl-1,3-dihydro-1-methyl-2H-1,4-benzo diazepin-2-one (4.7 g) in ethyl acetate (20 ml) until saturated. After 1.5 hours, the resulting precipitate (which was shown to be the undesired diastereomer; Rf=0.04, silica gel, ethyl acetate) was removed by filtration and the filtrate was concentrated under vacuum. Aqueous sodium carbonate solution (10%; 20 ml) was added to the remaining residue and products were extracted with ethyl acetate (3×25 ml), dried (Na$_2$SO$_4$) and concentrated. Flash chromatography of the residue (silica gel, ethyl acetate-methanol, 100% to 80:20) gave the title compound (1.66 g) (Rf=0.13, silica gel, ethyl acetate) as a solid; mp 100°–103° C.; [a]$_D^{23}$+32.7° (c=0.58, CH$_3$OH); $\delta_H$ (360 MHz, CDCl$_3$) 8.66 (1H, d, J=8.3 Hz), 7.58–7.47 (2H, m), 7.36–7.21 (7H, m) 5.36 (1H, d, J=8.3 Hz), 3.69 (1H, dd, J=9.8 and 4.1 Hz), 3.40 (3H, s), 3.28 (1H, dd, J=13.8 and 4.0 Hz), 2.79 (1H, dd, J=13.8 and 9.8 Hz), 2.74–2.62 (1H, m), 2.07–2.00 (1H, m), 1.92–1.84 (1H, m), 1.72–1.50 (4H, m), 1.39–1.00 (4H, m); m/z (CI) 419 (M⁺+1).

3. (+)-5-Cyclohexyl-1,3-dihydro-1-methyl-3(R)-[2(R)-(N-phenyl-thionocarbamoyl)amino-3-phenylpropionyl]amino-2H-1,4-benzodiazepin-2-one A solution of the product from the previous step (1.6 g) in anhydrous dichloromethane (10 ml) was treated with phenyl isothiocyanate (0.5 ml), and then heated on the steam bath for 30 minutes. The solvent was removed under vacuum and the residue purified by flash chromatography (silica gel, petroleum ether-ethyl acetate, 50:50) to give the title compound (2.1 g) as a solid; mp 129°–132° C.; [a]$_D^{25}$+27.3° (c=0.31, CH$_2$Cl$_2$); $d_H$ (360 MHz, CDCl$_3$) 7.79 (1H, s) 7.52–7.47 (2H, m), 7.36–7.18 (9H, m), 7.00 (1H, d, J=7.5 Hz), 6.71 (1H, d, J=7.0 Hz), 5.39–5.33 (1H, m), 5.23 (1H, d, J=7.3 Hz), 3.38 (3H, s), 3.41–3.24 (2H, m), 2.80–2.70 (1H, m), 2.00–1.93 (1H, m), 1.88–1.81 (1H, m), 1.69–1.45 (4H, m), 1.37–1.15 (3H, m), 1.07–0.95 (1H, m), m/z (CI) 553 (M⁻).

4. (+)-3(R)-Amino-5-Cyclohexyl-1,3-dihydro-1-methyl-2H-1,4-benzodiazepin-2-one

A solution of the product from the previous step (4.5 g) in trifluoroacetic acid (25 ml) was stirred at room temperature for 30 minutes. The solvent was removed under vacuum and the remaining residue was azeotroped with dichloromethane (2×20 ml) and toluene (2×20 ml). The residue was purified by flash chromatography (silica gel, dichloromethane-methanol-acetic acid-water, 90:10:0.1:0.1) to give an orange gum. This material was dissolved in ethyl acetate (150 ml), cooled to 0° C., and treated with 10% aqueous sodium carbonate (15 ml). After diluting with water (25 ml) and stirring for 1 minute, the organic layer was separated and the aqueous phase was re-extracted with ethyl acetate (2×50 ml). The combined organic solutions were dried (Na$_2$SO$_4$) and concentrated to give the title compound (1.56 g) as a solid; mp 133°–136° C.; [α]$_D^{23}$+33.2° (c=0.66, CH$_3$OH); the spectroscopic properties of this material ($^1$H-NMR and MS spectra) were identical to those described for its racemate (Intermediate 1).

The enantiomeric purity of the title compound was shown to be 99% e.e. by HPLC analysis using an a$_1$-AGP column (100 mm×4.6 mm id, 5 μm particle size) and eluting with 10 mM K$_2$HPO$_4$ (pH7)-acetonitrile (90:10) at 1 ml/minute; retention time 8.60 minutes (uv detection at 250 nm) (6.46 minutes retention time for its enantiomer).

EXAMPLE 1

N-[3(R,S)-5-Cyclohexyl-2,3-dihydro-1-methyl-2-oxo-1H-1,4-benzodiazepin-3-yl]-N'-[3-{(tetrazol-5-yl)aminomethyl}phenyl]urea 1. 3-[(Tetrazol-5-yl)aminomethyl]nitrobenzene A mixture of 3-nitrobenzaldehyde (1.51 g) and 5-aminotetrazole monohydrate (1.03 g)in absolute ethanol (30 ml) and glacial acetic acid (0.57 ml) was stirred at room temperature for 40 minutes and then refluxed under nitrogen for 5 hours 30 minutes. Solvents were removed under high vacuum and the remaining solid was suspended in absolute ethanol (50 ml) and treated at room temperature with solid sodium borohydride (1.2 g) over 20 minutes. After a further 15 hours of stirring, the solvent was removed under vacuum and the residue was dissolved in water (100 ml) and extracted with diethyl ether (2×30 ml). The basic aqueous phase was acidified to pH 2 with 2N hydrochloric acid and the precipitated solid was collected by filtration, washed with water, diethyl ether, and finally recrystallized from absolute ethanol to give the title compound (420 mg) as white needles; mp 208°–210° C.; $\delta_H$ (250 MHz, DMSO-d$_6$) 8.21 (1H, br s, Ar—H), 8.12 (1H, br d, J=9 Hz, Ar—H), 7.80 (1H, d, J=8 Hz, Ar—H), 7.70 (1H, br t, J=6.3 Hz, —NH—), 7.64 (1H, t, J=8 Hz, Ar—H), 4.53 (2H, d, J=6.3 Hz, —CH$_2$—); m/z (CI) 220 (M⁻).

2. 3-[(Tetrazol-5-yl)aminomethyl]aniline

A solution of the product from the previous step (350 mg) in a mixture of methanol (70 ml) and water (5 ml) was hydrogenated at 30 psi over 10% palladium on carbon (150 mg) for 4 minutes. The catalyst was filtered off, washed with methanol and solvents were removed under vacuum to give the title compound (288 mg) as a solid; $\delta_H$ (250 MHz, DMSO-$d_6$) 7.38 (1H, br t, J=6.3 Hz, —NH—), 6.94 (1H, t, J=7.7 Hz, Ar—H), 6.50 (1H, br s, Ar—H), 6.42 (2H, m, Ar—H), 5.00 (2H, br s, —NH$_2$), 4.23 (2H, d, J=6.3 Hz, Ar—CH$_2$—); m/z (CI) 189 (M$^+$+1).

3. N-[3(R,S)-5-Cyclohexyl-2,3-dihydro-1-methyl-2-oxo-1H-1,4-benzodiazepin-3-yl]-N'-[3-{(tetrazol-5-yl)aminomethyl}phenyl]urea To a stirred solution of Intermediate 2 (250 mg) in anhydrous dimethylformamide (3 ml) was added anhydrous triethylamine (82 µl) and the resulting yellow solution was stirred at room temperature, under a nitrogen atmosphere, for 5 minutes. A solution of 3-[(tetrazol-5-yl) aminomethyl] aniline (112 mg) in anhydrous dimethylformamide (3 ml) was added dropwise via cannula and the resulting solution was heated at 50°–55° C. for 5 hours. Solvents were removed under vacuum and the remaining residue was dissolved in a mixture of dichloromethane and methanol (95:5; 5 ml) and then precipitated by addition of diethyl ether (50 ml). The white solid was collected by filtration, purified by flash chromatography (silica gel, dichloromethane-methanol-acetic acid, 93:7:0.6; and dichloromethane-methanol, 90:10) and finally triturated with boiling ethyl acetate (2×10 ml) to give the title compound (80 mg) as a solid; mp 195°–202° C.; $\delta_H$ (360 MHz, DMSO-$d_6$) 8.97 (1H, s), 7.74 (1H, d, J=7.8 Hz), 7.63 (1H, br t, J=7.2 Hz), 7.54 (1H, d, J=7.7 Hz), 7.45 (1H, br t), 7.37 (1H, t, J=7.0 Hz), 7.28 (1H, s), 7.25 (2H, m), 7.16 (1H, t, J=7.7 Hz), 6.86 (1H, d, J=7.5 Hz), 5.05 (1H, d, J=8.3 Hz), 4.31 (2H, m), 3.31 (3H, s), 2.92 (1H, br t), 1.89 (1H, m), 1.77 (1H, m), 1.65–1.06 (7H, m), 0.91 (1H, m); m/z (FAB) 488 (M$^+$+1). (Found: C, 61.44; H, 6.00; N, 25.42. C$_{25}$H$_{29}$N$_9$O$_2$ requires: C, 61,59; H, 6.00; N, 25.86%).

EXAMPLE 2

N-[3(R,S)-5-Cyclohexyl-2,3-dihydro-1-methyl-2-oxo-1H-1,4-benzodiazepin-3-yl]-N'-[3-{(tetrazol-5-yl)amino}phenyl]urea

1.3-[(Tetrazol-5-yl)amino]nitrobenzene

To a stirred suspension of sodium azide (240 mg) and ammonium chloride (1.6 g) in anhydrous dimethylformamide (1.5 ml) was added dropwise via cannula a solution of 3-nitrophenyl cyanamide (500 mg) in anhydrous dimethylformamide (2.5 ml) and the resulting bright red mixture was heated at 165° C. for 16 hours under nitrogen. After being cooled to room temperature, water (60 ml) was added and the mixture was made alkaline with 2N sodium hydroxide. The basic aqueous solution was extracted with diethyl ether (1×30 ml) and then acidified with 5N hydrochloric acid. The precipitate was collected by filtration, washed with water (1×20 ml) and recrystallized from a mixture of water and ethanol (2:1; 30 ml)) to give the title compound (450 mg) as crystals; mp 228°–230° C.; $d_H$ (250 MHz, DMSO-$d_6$) 15.8 (br s, tetrazole —NH), 10.43 (1H, s, —NH—), 8.57 (1H, t, J=2.1 Hz, Ar—H), 7.90 (1H, m, Ar—H), 7.80 (1H, m, Ar—H), 7.61 (1H, t, J=8.2 Hz, Ar—H); m/z (CI) 206 (M$^-$).

2. 3-[(Tetrazol-5-yl)amino]aniline

A solution of the product from the previous step (410 mg) in a mixture of methanol (50 ml) and water (5 ml) was hydrogenated at 35 psi over 10% palladium on carbon (170 mg) for 4 minutes. The catalyst was filtered off, washed with methanol (2×10 ml) and solvents were removed under vacuum. The residue was azeotroped with methanol (20 ml) and further dried under high vacuum to give the title compound (324 mg) as a solid; $\delta_H$ (250 MHz, DMSO-$d_6$) 9.44 (1H, s, —NH—), 6.92 (1H, t, J=8.0 Hz, Ar—H), 6.76 (1H, s, Ar—H), 6.57 (1H, d, J=8.0 Hz, Ar—H), 6.17 (1H, d, J=8.0 Hz, Ar—H).

3. N-[3(R,S)-5-Cyclohexyl-2,3-dihydro-1-methyl-2-oxo-1H-1,4-benzodiazepin-3-yl]-N'-[3-{(tetrazol-5-yl)amino}phenyl]urea The title compound was prepared from Intermediate 2 and 3-[(tetrazol-5-yl)amino]aniline using a similar method to that described for Example 1 (step 3). The crude product was purified by flash chromatography (silica gel, dichloromethane-methanol-acetic acid, 92:8:05) and finally crystallized from a mixture of dimethylformamide and water; mp 250° C. (decomposition); $\delta_H$ (360 MHz, DMSO-$d_6$) 15.2 (br s, tetrazole —NH), 9.67 (1H, s), 9.03 (1H, s), 7.75 (1H, d, J=7.9 Hz), 7.63 (1H, t, J=7.9 Hz), 7.58–7.53 (2H, m), 7.37 (1H, t, J=7.5 Hz), 7.27 (1H, d, J=8.4 Hz), 7.13 (1H, t, J=7.6 Hz), 7.02 (2H, d, J=7.6 Hz), 5.07 (1H, d, J=8.4 Hz), 3.32 (3H, s), 2.93 (1H, m), 1.82 (1H, m), 1.78 (1H, m), 1.67–1.07 (7H, m), 0.90 (1H, m); m/z (FAB) 472 (M$^-$–1). (Found: C, 60.63; H, 5.67; N, 26.38.C$_{24}$H$_{27}$N$_9$O$_2$ requires: C, 60.87; H, 5.75; N, 26.62%).

EXAMPLE 3

N-[3(R,S)-5-Cyclohexyl-2,3-dihydro-1-methyl-2-oxo-1H-1,4-benzodiazepin-3-yl]-N'-[3-{N-methyl-N-(tetrazol-5-yl)amino}phenyl]urea

1. N-Methyl-3-nitrophenyl cyanamide

To a cooled (–20° C.) and stirred solution of 3-nitrophenyl cyanamide (1 g) in a mixture of anhydrous tetrahydrofuran and anhydrous dimethylformamide (3:1; 20 ml) was added sodium hydride (60% dispersion in oil; 294 mg) in one portion, under a nitrogen atmosphere. After 8 minutes of stirring at –20° C., methyl iodide (1.14 ml) was added and the red mixture was allowed to warm to room temperature and diluted with anhydrous dimethylformamide (5 ml). After a further 45 minutes of stirring, water (75 ml; CAUTION! hydrogen evolution) was added and products were extracted with ethyl acetate (2×100 ml). The combined organic phases were washed with brine (1×50 ml), dried (MgSO$_4$) and concentrated. The remaining solid was dissolved in ethyl acetate (30 ml) and hexane (100 ml) was added to give the title compound (880 mg) as fine needles; $\delta_H$ (250 MHz, DMSO-$d_6$) 7.98 (1H, m, Ar—H), 7.85 (1H,t, J=2.2 Hz, Ar—H), 7.73 (1H, t, J=7.7 Hz, Ar—H), 7.60 (1H, m, Ar—H), 3.45 (3H, s, —NMe);m/z (CI) 177 (M$^-$).

2. 3-[(N-Methyl-N-(tetrazol-5-yl)amino]nitrobenzene

The title compound was prepared from N-methyl-3-nitrophenyl cyanamide using a similar method to that described for Example 2 (step 1); mp 196°–198° C. (ethanol-water, 1:3); $\delta_H$ (360 MHz, DMSO-$d_6$) 8.43 (1H, t, J=2.3 Hz, Ar—H), 7.94 (2H, m, Ar—H), 7.68 (1H, t, J=8.3 Hz, Ar—H), 3.56 (3H, s, —NMe); m/z (CI) 220 (M$^-$).

3. 3-[(N-Methyl-N-(tetrazol-5-yl)amino]aniline

The title compound was prepared from 3-[(N-methyl-N-(tetrazol-5-yl)amino]nitrobenzene using a similar method to that described for Example 2 (step 2); white solid; $\delta_H$ (250 MHz, DMSO-$d_6$) 7.03 (1H, t, J=8.0HZ, Ar—H), 6.54 (1H, t, J=2.1 Hz, Ar—H), 6.47 (1H, ddd, J=7.9, 2.2 and 0.9 Hz, Ar—H), 6.39 (1H, ddd, J=8.0, 2.1 and 0.9 Hz, Ar—H), 3.36 (3H, s, —NMe); m/z (CI) 190 (M$^-$).

4. N-[3(R,S)-5-Cyclohexyl-2,3-dihydro-1-methyl-2-oxo-1H-1,4-benzodiazepin-3-yl]-N'-[3-{N-methyl-N-(tetrazol-5-yl)amino}phenyl]urea To a cooled (0° C.) and stirred cloudy solution of 3-[(N-methyl-N-(tetrazol-5-yl)amino]aniline (254 mg) in anhydrous tetrahydrofuran (30 ml) was added solid triphosgene (132 mg) in one portion under a nitrogen atmosphere. The resulting mixture was stirred for 5 minutes before anhydrous triethylamine (0.6 ml) was added and it was allowed to warm to 15° C. over 15 minutes. A solution of Intermediate 1 (248 mg) in anhydrous tetrahydrofuran (5 ml) was then added dropwise via cannula over 5 minutes and the mixture was stirred at room temperature for 2 hours before it was diluted with anhydrous dimethylformamide (15 ml). After a further 1.5 hours of stirring, a white precipitate was removed by filtration and solvents were evaporated under vacuum. The remaining residue was partitioned between ethyl acetate (250 ml) and 10% aqueous citric acid (2×45 ml) and the organic phase was washed with brine (1×45 ml), then dried ($Na_2SO_4$) and concentrated. Flash chromatography of the residue (silica gel, dichloromethane-methanol, 90:10) gave the title compound (380 mg) as a solid; mp 231°–235° C. (methanol); $\delta_H$ (360 MHz, DMSO-$d_6$) 15.2 (br s, tetrazole —NH), 9.11 (1H, s), 7.74 (1H, d, J=7.7 Hz), 7.63 (1H, t, J=8.4 Hz), 7.54 (1H, d, J=8.2 Hz), 7.48 (1H, br s), 7.37 (1H, t, J=7.2 Hz), 7.29 (1H, d, J=8.4 Hz), 7.25 (1H, t, J=8.0 Hz), 7.12 (1H, br d, J=8.9 Hz), 6.94 (1H, br d, J=8.0 Hz), 5.06 (1H, d, J=8.4 Hz), 3.39 (3H, s), 3.34 (3H,s), 2.93 (1H, m), 1.90 (1H, m), 1.78 (1H,m), 1.68–1.08 (7H,m), 0.89 (1H,m); m/z (CI) 488 ($M^-$+1). (Found: C, 60,89; H, 5.94; N, 25.53. $C_{25}H_{29}N_9O_2 \times 0.25\ H_2O$ requires: C, 61.02; H, 6.04; N, 25.62%).

EXAMPLE 4

(+)-N-[3(R)-5-Cyclohexyl-2,3-dihydro-1-methyl-2-oxo-1H-1,4-benzodiazepin-3-yl]-N'-[3-{N-methyl-N-(tetrazol-5-yl)amino}phenyl]urea To a cooled (0° C.) and stirred milky solution of 3-[N-methyl-N-(tetrazol-5-yl)amino]aniline (230 mg) in anhydrous tetrahydrofuran (30 ml) was added solid triphosgene (120 mg) in one portion, under a nitrogen atmosphere. After 5 minutes of stirring, anhydrous triethylamine (505 µl) was added dropwise and the mixture was allowed to warm to 17° C. over 15 minutes. The reaction mixture was recooled to 0° C. and a solution of Intermediate 3 (225 mg) in anhydrous tetrahydrofuran (5 ml) was added dropwise via cannula over 4 minutes. After being stirred at 0° C. for 15 minutes, the mixture was allowed to warm to room temperature and stirred for a further 2 hours before a white precipitate was removed by filtration and the solvent was evaporated under reduced pressure. The remaining residue was partitioned between ethyl acetate (200 ml) and 10% aqueous citric acid (2×40 ml) and the organic phase was then washed with brine (1×40 ml), dried ($Na_2SO_4$) and concentrated to a yellow solid. Flash chromatography (silica gel, dichloromethane-methanol, 90:10) afforded the title compound (336 mg) as a solid; mp 222°–225° C. (methanol; decomposition); $[\alpha]_D^{23}$+15.9° (c=0.71, dimethylformamide); the spectroscopic properties ($^1$H-NMR and MS spectra) of this material were identical to those described for its racemate (Example 3). (Found: C, 61.92; H, 5.87; N, 25.96. $C_{25}H_{29}N_9O_2$ requires: C, 61.59; H, 6.00; N, 25.86%).

The enantiomeric purity of the title compound was shown to be greater than 99% e.e. by HPLC analysis using a PIRKLE (S)-DNBL ((S)-3,5-dinitrobenzoylleucine) column (250 mm×4.6 mm id, 5 µm particle size) and eluting with dichloromethane-methanol-acetic acid (94.2:5:0.8) at 1 ml/minute; retention time 5.66 minutes (uv detection at 250 mm) (10.21 minutes retention time for its enantiomer).

EXAMPLE 5

(+)-N-[3(R)-5-Cyclohexyl-2,3-dihydro-1-methyl-2-oxo-1H-1,4-benzodiazepin-3-yl]-N'-[3-{(tetrazol-5-yl)amino}phenyl]urea The title compound was prepared from Intermediate 3 and 3-[(tetrazol-5-yl)amino]aniline using a similar method to that described for Example 4, except that anhydrous acetonitrile was used as the reaction solvent; the crude product was purified by flash chromatography (silica gel, dichloromethane-methanol, 93:7 to 80:20) and recrystallized from methanol; mp 190°–193° C.; $[\alpha]_D^{25}$+8.4° (c=0.50, dimethylformamide); the spectroscopic properties ($^1$H-NMR and MS spectra) of this material were identical to those described for its racemate (Example 2). (Found: C, 59.78; H, 5.98; N, 25.68. $C_{24}H_{27}N_9O_2 \times 0.6H_2O$ requires: C, 59.52; H, 5.87; N, 26.03%).

The enantiomeric purity of the title compound was shown to be 99% e.e. by HPLC analysis using the conditions described in Example 4 except that dichloromethane-methanol-acetic acid (83.4:15:1.6) was used as the mobile phase; retention time 6.85 minutes (10.37 minutes for its enantiomer).

EXAMPLE 6

(+)-N-[3(R)-5-Cyclohexyl-2,3-dihydro-1-methyl-2-oxo-1H-1,4-benzodiazepin-3-yl]-N'-[3-{(tetrazol-5-yl)aminomethyl}phenyl]urea The title compound was prepared from Intermediate 3 and 3-[(tetrazol-5-yl)aminomethyl]aniline using a similar method to that described for Example 4, except that anhydrous acetonitrile was used instead of tetrahydrofuran; the crude product was purified by flash chromatography (silica gel, dichloromethane-methanol, 95:5 to 90:10) and recrystallized from a mixture of methanol and ethyl acetate; mp 175°–178° C.; $[\alpha]_D^{24}$+17.4° (c=0.50, dimethylformamide); the spectroscopic properties of this material ($^1$H-NMR and MS spectra) were identical to those described for its racemate (Example 1).

The enantiomeric purity of the title compound was shown to be 92.5% e.e. by HPLC analysis using the conditions described in Example 4, except that dichloromethane-methanol-acetic acid (89.2:10:0.8) was used as the mobile phase; retention time 6.9 minutes (12.1 minutes for its enantiomer).

EXAMPLE 7

(+)-N-[3(R)-2,3-Dihydro-1-methyl-2-oxo-5-phenyl-1H-1,4-benzodiazepin-3-yl]-N'-[3-{N-methyl-N-(tetrazol-5-yl)amino}phenyl]urea The title compound was prepared from 3(R)-amino-1,3-dihydro-1-methyl-5-phenyl-2H-1,4-benzodiazepin-2-one (*J. Org. Chem.* 1987, 52, 955, 3232) and 3-[N-methyl-N-(tetrazol-5-yl)amino]aniline using a similar method to that described for Example 4. The crude product was purified by flash chromatography (silica gel, dichloromethane-methanol, 95:5 to 93:7) and recrystallized from methanol; mp 205°–210° C.; $[\alpha]_D^{25}$+65.2° (c=0.5, dimethylformamide); $\delta_H$ (360 MHz, DMSO-$d_6$) 9.19 (1H, s), 7.78–7.71 (1H, m), 7.67 (1H, d, J=7.9 Hz), 7.56–7.42 (7H, m), 7.39–7.32 (2H,m), 7.27 (1H, t, J=8.1HZ), 7.15 (1H, br d, J=9.0 Hz), 6.97–6.94 (1H, m), 5.24 (1H, d, J=8.3 Hz), 3.41 (6H, s). (Found: C, 61.38; H, 4.77; N, 25.42. $C_{25}H_{23}N_9O_2 \times 0.5\ H_2O$ requires: C, 61.21; H, 4.93; N, 25.70%).

Examples 8 and 9 were prepared from 3(R)-amino-1,3-dihydro-1-methyl-5-phenyl-2H-1,4-benzodiazepin-2-one and the appropriate 3-substituted anilines (Example 2, step 2; and Example 1, step 2) using a similar method to that described for Example 4, except that tetrahydrofuran was replaced by anhydrous acetonitrile.

EXAMPLE 8

(+)-N-[3(R)-2,3-Dihydro-1-methyl-2-oxo-5-phenyl-1H-1,4-benzodiazepin-3-yl]-N'-[3-{(tetrazol-5-yl)amino}phenyl]urea The crude product was purified by flash chromatography (silica gel, dichloromethane-methanol, 90:10) and recrystallized from methanol to give the title compound as a white solid; mp 233°–243° C. $[\alpha]_D^{25}$+69.6° (c=0.5, dimethylformamide); $\delta_H$ (360 MHz, DMSO-$d_6$) 9.70 (1H,s), 9.11 (1H, s), 7.77–7.71 (1H, m), 7.67 (1H, d, J=8.0 Hz), 7.61 (1H, m), 7.58–7.43 (6H, m), 7.40–7.32 (2H,m), 7.15 (1H, t, J=8.0 Hz), 7.10–7.03 (2H, m), 5.25 (1H, d, J=8.4 Hz), 3.41 (3H, s). (Found: C, 61.78; H, 4.59; N, 26.55. $C_{24}H_{21}N_9O_2$× 0.1 $H_2O$ requires: C, 61.43; H, 4.55; N, 26.86%).

EXAMPLE 9

(+)-N-[3(R)-2,3-Dihydro-1-methyl-2-oxo-5-phenyl-1H-1,4-benzodiazepin-3-yl]-N'-[3-{(tetrazol-5-yl)aminomethyl}phenyl]urea The crude product was purified by flash chromatography (silica gel, dichloromethane-methanol, 90:10; and dichloromethane-methanol, 95:5 to 90:10) and finally recrystallized from methanol to give the title compound as a white solid; mp 190°–195° C.; $[\alpha]_D^{25}$+75.4° (c=0.5, dimethylformamide); $\delta_H$ (360 MHz, DMSO-$d_6$) 9.06 (1H, s), 7.76–7.71 (1H, m), 7.67 (1H, d, J=8.0 Hz), 7.59–7.43 (7H, m), 7.40–7.28 (4H, m), 7.18 (1H, t, J=7.9 Hz), 7.88 (1H, d, J=7.6 Hz), 5.23 (1H, d, J=8.3 Hz), 4.33 (2H, d, J=5.7 Hz), 3.40 (3H, s). (Found: C, 60.44; H, 4.70; N, 25.49. $C_{25}H_{23}N_9O_2$×$H_2O$ requires: C, 60.11; H, 5.04; N, 25.49%).

EXAMPLE 10

(+)-N-[3(R)-5-Cyclohexyl-2,3-dihydro-1-methyl-2-oxo-1H-1,4-benzodiazepin-3-yl]-N'-[4-methyl-3-{(tetrazol-5-yl)amino}phenyl]urea 1. 4-Methyl-3-[(tetrazol-5-yl)amino]nitrobenzene The title compound was prepared from 2-methyl-5-nitrophenyl cyanamide using a similar method to that described for Example 2 (Step 1); mp 245°–249° C. (methanol-water); $\delta_H$ (250 MHz, DMSO-$d_6$) 9.34 (1H, s, —NH—), 8.80 (1H, d, J=2.4 Hz, Ar—H), 7.82 (1H, dd, J=8.3 and 2.4 Hz, Ar—H), 7.49 (1H, d, J=8.3 Hz, Ar—H), 2.41 (3H, s, —Me); m/z (CI) 220 (M⁻).

2. 4-Methyl-3-[(tetrazol-5-yl)amino]aniline

The title compound was prepared from 4-methyl-3-[(tetrazol-5-yl)amino]nitrobenzene using the conditions described for Example 2 (Step 2); solid; $\delta_H$ (360 MHz, DMSO-$d_6$) 8.11 (1H, s, —NH—), 6.84–6.79 (2H, m, Ar—H), 6.24 (1H, dd, J=8.0 and 2.2 Hz, Ar—H), 2.05 (3H, s, —Me); m/z (CI) 191 (M⁺+1).

3. (+)-N-[3(R)-5-Cyclohexyl-2,3-dihydro-1-methyl-2-oxo-1H-1,4-benzodiazepin-3-yl]-N'-[4-methyl-3-{(tetrazol-5-yl)amino}phenyl]urea The title compound was prepared from Intermediate 3 and 4-methyl-3-[(tetrazol-5-yl)amino]aniline using a similar method to that described for Example 4; mp 190–193° C. (methanol-dichloromethane); $[\alpha]_D^{25}$+12.2° (c=0.29, dimethylformamide); $\delta_H$ (360 MHz, DMSO-$d_6$) 8.98 (1H, s), 8.75 (1H, s), 7.74 (1H, d, J=7.9 Hz), 7.66–7.59 (2H, m), 7.54 (1H, d, J=7.6 Hz), 7.37 (1H, t, J=7.0 Hz), 7.21 (1H, d, J=8.5 Hz), 7.09–7.01 (2H, m), 5.05 (1H, d, J=8.5 Hz), 3.32 (3H, s), 2.98–2.87 (1H, m), 2.14 (3H, s), 1.96–1.86 (1H, m), 1.81–1.72 (1H, m), 1.64–1.06 (7H, m), 0.96–0.84 (1H, m); m/z (CI) 487 (M⁻). (Found: C, 61.73; H, 6.08; N, 26.02. $C_{25}H_{29}N_9O_2$ requires: C, 61.57; H, 6.00; N, 25.86%).

EXAMPLE 11

(+)-N-[3(R)-5-Cyclohexyl-2,3-dihydro-1-methyl-2-oxo-1H-1,4-benzodiazepin-3-yl]-N'-[4-methyl-3-{N-methyl-N-(tetrazol-5-yl)amino}phenyl]urea 1. N-Methyl-N-(2-methyl-5-nitrophenyl)cyanamide The title compound was prepared from 2-methyl-5-nitrophenyl cyanamide using a similar method to that described for Example 3 (Step 1) except that the crude product was purified by flash chromatography (silica gel, hexane-ethyl acetate, 60:40); solid; $\delta_H$ (250 MHz, CDCl₃) 8.09–8.03 (2H, m, Ar—H), 7.43 (1H, dd, J=8.8 and 0.7 Hz, Ar—H), 3.40 (3H, s, —NMe), 2.55 (3H, s, —Me); m/z (CI) 191 (M⁻).

2. 4-Methyl-3-[N-methyl-N-(tetrazol-5-yl)amino]nitrobenzene

The title compound was prepared from the product from the previous step using a similar method to that described for Example 2 (Step 1); yellow solid; mp 201°–205° C. (water); $d_H$ (250 MHz, DMSO-$d_6$) 8.24 (1H, d, J=2.4 Hz, Ar—H), 8.15 (1H, dd, J=8.4 and 2.4 Hz, Ar—H), 7.65 (1H, d, J=8.4 Hz, Ar—H), 3.40 (3H, s, —NMe), 2.24 (3H, s, —Me); m/z (CI) 234 (M⁻).

3. 4-Methyl-3-[N-methyl-N-(tetrazol-5-yl)amino]aniline

The title compound was prepared from 4-methyl-3-[N-methyl-N-(tetrazol-5-yl)amino]nitrobenzene using a similar method to that described for Example 2 (Step 2); white solid; $\delta_H$ (250 MHz, DMSO-$d_6$) 6.97 (1H, d, J=8.1 Hz, Ar—H), 6.50 (1H, dd, J=8.1 and 2.3 Hz, Ar—H), 6.41 (1H, d, J=2.3 Hz, Ar—H), 3.25 (3H, s, —NMe), 1.92 (3H, s, —Me); m/z (CI) 205 (M⁺+1).

4. (+)-N-[3(R)-5-Cyclohexyl-2,3-dihydro-1-methyl-2-oxo-1H-1,4-benzodiazepin-3-yl]-N'-[4-methyl-3-{N-methyl-N-(tetrazol-5-yl)amino}phenyl]urea The title compound was prepared from Intermediate 3 and 4-methyl-3-[N-methyl-N-(tetrazol-5-yl)amino]aniline using a similar method to that described for Example 4; the crude product was purified by flash chromatography (silica gel, dichloromethane-methanol, 94:6) and crystallized from methanol-dichloromethane; mp 223°–225° C.; $[\alpha]_D^{25}$+20.3° (c=0.34, dimethylformamide); $\delta_H$ (360 MHz, DMSO-$d_6$) 9.03 (1H, s), 7.74 (1H, d, J=6.7 Hz), 7.63 (1H, dt, J=8.4 and 1.4 Hz), 7.54 (1H, d, J=7.5 Hz), 7.40–7.33 (2H, m), 7.26 (1H, d, J=8.4 Hz), 7.20–7.13 (2H, m), 5.04 (1H, d, J=8.4 Hz), 3.31 (3H, s), 3.27 (3H, s), 2.98–2.89 (1H, m), 2.01 (3H, s), 1.94–1.85 (1H, m), 1.82–1.73 (1H, m), 1.66–1.06 (7H, m), 0.96–0.84 (1H, m); m/z (CI) 501 (M⁻). (Found: C, 62.11; H, 6.40; N, 24.99. $C_{26}H_{31}N_9O_2$ requires: C, 62.26; H, 6.23; N, 25.13%).

Examples 12 and 13 were prepared from 3(R)-amino-1,3-dihydro-1-methyl-5-phenyl-2H-1,4-benzodiazepin-2-one and the appropriate anilines (Example 10, Step 2; and Example 11, Step 3), using a similar method to that described for Example 4.

EXAMPLE 12

(+)-N-[3(R)-2,3-Dihydro-1-methyl-2-oxo-5-phenyl-1H-1,4-benzodiazepin-3-yl]-N'-[4-methyl-3-{(tetrazol-5-yl)amino}phenyl]urea The crude product was purified by flash chromatography (silica gel, dichloromethane-methanol, 95:5 to 90:10) and recrystallized from methanol to give the title compound; mp 198°–201° C.; $[\alpha]_D^{25}$+63.4° (c=0.5, dimethylformamide); $\delta_H$ (360 MHz, DMSO-$d_6$) 9.06 (1H, s), 8.78 (1H, s), 7.76–7.62 (3H, m), 7.58–7.32 (8H, m), 7.11 (1H, dd, J=8.3 and 2.0 Hz), 7.05 (1H, d, J=8.3 Hz), 5.23 (1H, d, J=8.4 Hz), 3.40 (3H, s), 2.16 (3H, s); m/z (CI) 481 (M⁻). (Found: C, 61.12; H, 4.99; N, 25.52. $C_{25}H_{23}N_9O_2 \times 0.5H_2O$ requires: C, 61.21; H, 4.93; N, 25.70%).

EXAMPLE 13

(+)-N-[3(R)-2,3-Dihydro-1-methyl-2-oxo-5-phenyl-1H-1,4-benzodiazepin-3-yl]-N'-[4-methyl-3-{N-methyl-N-(tetrazol-5-yl)amino}phenyl]urea The crude product was purified by flash chromatography (silica gel, dichloromethane-methanol, 97:3 to 93:7) and recrystallized from methanol-dichloromethane to give the title compound; mp 217°–225° C.; $[\alpha]_D^{25}$+68.6° (c=0.5, dimethylformamide); $\delta_H$ (360 MHz, DMSO-$d_6$) 9.11 (1H, s), 7.77–7.70 (1H, m), 7.66 (1H, d, J=7.7 Hz), 7.56–7.30 (9H, m), 7.24–7.18 (2H, m), 5.22 (1H, d, J=8.3 Hz), 3.40 (3H, s), 3.28 (3H, s), 2.03 (3H, s); m/z (CI) 495 (M⁻). (Found: C, 62.32; H, 5.12; N, 25.25. $C_{26}H_{25}N_9O_2 \times 0.2H_2O$ requires: C, 62.56; H, 5.13; N, 25.26%).

EXAMPLE 14

(+)-N-[3(R)-2,3-Dihydro-1-methyl-2-oxo-5-phenyl-1H-1,4-benzodiazepin-3-yl]-N'-[1-(tetrazol-5yl)indolin-6-yl]urea

1. 1-Cyano-6-nitroindoline

To a cooled (4° C.) and stirred solution of 6-nitroindoline (3.04 g) in a mixture of glacial acetic acid (22 ml), water (11 ml) and absolute ethanol (23 ml) was added solid cyanogen bromide (2.93 g) followed by 1N aqueous sodium hydroxide solution (25 ml) over 3 minutes. The mixture was then allowed to warm to room temperature, stirred for a further 21 hours and the solid formed was collected by filtration, washed with water and dried over phosphorous pentoxide to give the title compound (2.94 g) as a solid; $\delta_H$ (250 MHz, DMSO-$d_6$) 7.90 (1H, dd, J=8.1 and 2.2 Hz), 7.55–7.50 (2H, m), 4.23 (2H, t, J=8.4 Hz), 3.30 (2H, t, J=8.4 Hz); m/z (CI) 189 (M⁻).

2. 6-Nitro-1-(tetrazol-5-yl)indoline

The title compound was prepared from 1-cyano-6-nitroindoline using a similar method to that described for Example 2 (Step 1), except that the crude precipitate was purified by flash chromatography (silica gel, dichloromethane-methanol-acetic acid, 90:10:0.70 to 80:20:0.7) and finally recrystallized from methanol-water (2.5:1); mp 262°–270° C.; $\delta_H$ (250 MHz, DMSO-$d_6$) 8.60 (1H, d, J=2.2 Hz), 7.83 (1H, dd, J=8.1 and 2.2 Hz), 7.50 (1H, d, J=8.1 Hz), 4.21 (2H, t, J=8.5 Hz), 3.40 (2H, t, J=8.5 Hz); m/z (CI) 232 (M⁻).

3. 6-Amino-1-(tetrazol-5-yl)indoline

The title compound was prepared from 6-nitro-1-(tetrazol-5-yl)indoline using the conditions described for Example 2 (Step 2); solid; $\delta_H$ (250 MHz, DMSO-$d_6$) 7.24 (1H, d, J=2.0 Hz), 6.86 (1H, d, J=7.9 Hz), 6.13 (1H, dd, J=7.9 and 2.0 Hz), 3.98 (2H, t, J=8.3 Hz), 3.07 (2H, t, J=8.3 Hz); m/z (CI) 203 (M⁺+1).

4. (+)-N-[3(R)-2,3-Dihydro-1-methyl-2-oxo-5-phenyl-1H-1,4-benzodiazepin-3-yl]-N'-[1-(tetrazol-5-yl)indolin-6-yl]urea The title compound was prepared from 3(R)-amino-1,3-dihydro-1-methyl-5-phenyl-2H-1,4-benzodiazepin-2-one and 6-amino-1-(tetrazol-5-yl)indoline using a similar method to that described for Example 4. The crude product was purified by flash chromatography (silica gel, dichloromethane-methanol, 97:3 to 90:10) and recrystallized from a mixture of methanol and water (10:1); mp 215°–220° C.; $[\alpha]_D^{25}$+64.8° (c=0.5, dimethylformamide); $\delta_H$ (360 MHz, DMSO-$d_6$) 9.16 (1H, s), 7.96 (1H, s), 7.78–7.71 (1H, m), 7.68 (1H, d, J=8.1 Hz), 7.58–7.34 (8H, m), 7.12–7.02 (2H, m), 5.26 (1H, d, J=8.4 Hz), 4.04 (2H, t, J=8.7 Hz), 3.41 (3H, s), 3.18 (2H, t, J=8.7 Hz); m/z (CI) 493 (M⁻). (Found: C, 59.68; H, 4.73; N, 24.08. $C_{26}H_{23}N_9O_2 \times 1.6 H_2O$ requires: C, 59.78; H, 5.06; N, 24.13%).

EXAMPLE 15

(+)-N-[3(R,S)-2,3-Dihydro-1,3-dimethyl-2-oxo-5-phenyl-1H-1,4-benzodiazepin-3-yl]-N'-[3-{(tetrazol-5yl)aminomethyl}phenyl]urea

1. 3(R,S)-Amino-1,3-dimethyl-5-phenyl-2H-1,4-benzodiazepin-2-one

A mixture of 3(R,S)-amino-1,3-dihydro-1-methyl-5-phenyl-2H-1,4-benzodiazepin-2-one (J. Org. Chem., 1987, 52, 3232) (1 g), benzaldehyde (408 mg) and anhydrous magnesium sulphate (3 g) in anhydrous dichloromethane (25 ml) was stirred at room temperature for 21 hours, under nitrogen. 4 Å Molecular sieves (2 g) were added to the above mixture and it was refluxed for 19 hours and finally stirred at room temperature for a further 23 hours. Solids were filtered off, washed with anhydrous dichloromethane (15 ml) and the solvent was removed under vacuum. The remaining residue was azeotroped with toluene (2×15 ml) and further dried under high vacuum to give a yellow foam. This material was dissolved in anhydrous tetrahydrofuran (10 ml) and it was added via cannula to a cooled (−72° C.) and stirred solution of sodium bis(trimethylsilyl)amide (1M in tetrahydrofuran; 4.2 ml) in anhydrous tetrahydrofuran (10 ml) over 7 minutes, under a nitrogen atmosphere. The resulting dark blue solution was stirred at −72° C. for 5 minutes before iodomethane (0.27 ml) was added dropwise and stirring was continued at −70° C. for 2 hours and at room temperature for 17 hours. Brine (20 ml) was added and the organic solvent was removed under vacuum. The aqueous residue was diluted with 2N hydrochloric acid (10 ml) and methanol (5 ml) and it was stirred at room temperature for 10 minutes before it was extracted with diethyl ether (2×25 ml). The acidic aqueous solution was basified with 2N sodium hydroxide and products were extracted with ethyl acetate (3×65 ml). The combined organic solutions were washed with brine (1×25 ml), dried ($Na_2SO_4$) and concentrated. Flash chromatography (silica gel, dichloromethane-methanol, 92:8) of the residue gave the title compound (577 mg) as a solid; $\delta_H$ (250 MHz, CDCl$_3$) 7.66–7.26 (8H, m, Ar—H), 7.15 (1H, dt, J=8.0 and 1.1 Hz, Ar—H), 3.52 (3H, s, —NMe), 1.00 (3H, s, —Me); m/z (CI) 280 (M⁺+1).

2. N-[3-(R,S)-2,3-Dihydro-1,3-dimethyl-2-oxo-5-phenyl-1H-1,4-benzodiazepin-3-yl]-N'-[3-{(tetrazol-5-yl)aminomethyl}phenyl]urea To a cooled (0° C.) and stirred solution of 3-[(tetrazol-5-yl)aminomethyl]aniline (Example 1, Step 2) (421 mg) in anhydrous acetonitrile (180 ml) was added triphosgene (219 mg) in one portion, under a nitrogen atmosphere. After 5 minutes of stirring, anhydrous triethylamine (924 µl) was added dropwise and the mixture was allowed to warm to 15° C. over 20 minutes. A solution of 3(R,S)-amino-1,3-dihydro-1,3-dimethyl-5-phenyl-2H-1,4-benzodiazepin-2-one (415 mg) in anhydrous acetonitrile (20 ml) was added dropwise via cannula over 5 minutes and the resulting mixture was stirred at room temperature for 3 hours 20 minutes before it was diluted with anhydrous dimethylformamide (30 ml). After 15 minutes, solvents were removed under vacuum and the residue was diluted with ethyl acetate (300 ml), washed with 10% aqueous citric acid (2×50 ml), brine (2×50 ml), dried (MgSO$_4$) and concentrated. Flash chromatography (silica gel, dichloromethane-methanol-acetic acid, 92:8:0.5) of the residue gave impure product which was further purified by preparative TLC (silica gel, dichloromethane-methanol, 90:10) and finally crystallized from a mixture of ethanol and diethyl ether; mp 180° C. (softens and decomposes); m/z (FAB) 494 (M$^+$−1). (Found: C, 59.90; H, 5.03; N, 24.27. C$_{26}$H$_{25}$N$_9$O$_2$×1.4 H$_2$O requires: C, 59.97; H, 5.38; N, 24.21%).

EXAMPLE 16

N-[3(R,S)-1-tert-Butyl-2,3-dihydro-2-oxo-5-phenyl-1H-1,4-benzodiazepin-3-yl]-N'-[4-methyl-3-{(tetrazol-5-yl)amino}phenyl]urea 1. 2(tert-Butylamino)benzophenone A mixture of 2-aminobenzophenone (20 g), tert-butyl alcohol (100 ml) and 10M ethanolic hydrogen chloride (10 ml) was heated in a steel bomb at 120° C. for 20 minutes. After being cooled to room temperature, solvents were removed under vacuum and the residue was purified by flash chromatography (silica gel, hexane-toluene, 30:70) to give the title compound (5.62 g) as an oil, δ$_H$ (360 MHz, CDCl$_3$) 8.95 (1H, s), 7.61–7.28 (7H, m), 7.01 (1H, d, J=8.6 Hz), 6.48 (1H, t, J=7.4 Hz), 1.49 (9H, s); m/z (CI) 253 (M$^-$).

2. 2-[N-(2-chloroacetyl)-N-tert-butylamino]benzophenone

A mixture of 2-(tert-butylamino)benzophenone (7.5 g) and chloroacetyl chloride (20 ml) in anhydrous toluene (250 ml) was refluxed for 2 hours under nitrogen. Solvents were removed under vacuum and the remaining residue was dissolved in ethyl acetate (250 ml), washed with 5% sodium bicarbonate solution, dried (MgSO$_4$) and concentrated. Flash chromatography of the residue (silica gel, toluene-ethyl acetate, 99:1 to 95:5) gave the title compound (7 g) as a solid; δ$_H$ (360 MHz, CDCl$_3$) 7.87–7.84 (2H, m), 7.68–7.46 (6H, m), 7.36 (1H, d, J=7.7 Hz), 4.05 (1H, d, J=13.2 Hz), 3.72 (1H, d, J=13.2 Hz), 1.27 (9H, s); m/z (CI) 329 (M$^-$).

3. 1-tert-Butyl-1,3-dihydro-5-phenyl-2H-1,4-benzodiazepin-2-one

A mixture of the product from the previous step (6.62 g), sodium azide (1.44 g) and sodium iodide (480 mg) in anhydrous dimethylformamide (120 ml) was stirred at 50° C. for 3 days under a nitrogen atmosphere. The solvent was removed under vacuum and the residue was partitioned between water (150 ml) and dichloromethane (4×50 ml). The organic extracts were dried (MgSO$_4$) and concentrated. The residue was triturated with petroleum ether (60–80) to give the intermediate azido compound (6.67 g).

To a solution of the previous azide (6.93 g) in anhydrous tetrahydrofuran (200 ml) was added portionwise triphenylphosphine (24 g) and the resulting mixture was stirred overnight at room temperature under a nitrogen atmosphere. The solvent was then removed under vacuum and the residue purified by flash chromatography (silica gel, hexane-ethyl acetate, 80:20 to 50:50) to give the title compound (5.88 g) as a solid; δ$_H$ (360 MHz, CDCl$_3$) 7.71–7.68 (2H, m), 7.50–7.34 (5H, m), 7.28–7.20 (2H, m), 4.57 (1H, d, J=11.3 Hz), 3.70 (1H, d, J=11.3 Hz), 1.44 (9H, s); m/z (CI) 293(M$^+$+1).

4. 1-tert-Butyl -1,3-dihydro-3-oximido-5-phenyl-2H-1,4-benzodiazepin-2-one

To a cooled (0° C.) and stirred solution of 1-tert-butyl-1,3-dihydro-5-phenyl-2H-1,4-benzodiazepin-2-one (4.33 g) in anhydrous toluene (200 ml) was added potassium tert-butoxide (4.38 g) in one portion. After 30 minutes of stirring, isopentyl nitrite (2.3 ml) was added dropwise over 5 minutes and the mixture was stirred for further 20 minutes. Aqueous citric acid (10%; 250 ml) was added and the organic phase was separated. The aqueous layer was extracted with diethyl ether (3×50 ml) and the combined organic phases were dried and concentrated. The residue was triturated with hexane to give a yellow solid which was heated with hexane-ethyl acetate, re-cooled and the solid was collected by filtration. The mother liquors from both triturations were purified by flash chromatography (silica gel, dichloromethane-methanol, 97:3) to give a total combined mass of 4.32 g of the title compound; m/z (CI) 321(M$^-$).

5. 3-(R,S)-Amino-1-tert-butyl-1,3-dihydro-5-phenyl-2H-1,4-benzodiazepin-2-one

A mixture of 1-tert-butyl-1,3-dihydro-3-oximido-5-phenyl-2H-1,4-benzodiazepin-2-one (1.16 g) and 5% ruthenium on carbon (540 mg) in methanol (20 ml) was hydrogenated at 48 psi of pressure while maintaining a temperature of 80° C., for 18 hours. After cooling, the catalyst was filtered off and the solvent was removed under vacuum. The residue was purified by flash chromatography (silica gel, dichloromethane-methanol, 95:5 to 90:10) to give the title compound (322 mg) as a solid; δ$_H$ (250 MHz, CDCl$_3$) 7.72–7.67 (2H, m), 7.52–7.22 (7H, m), 4.38 (1H, s), 1.43 (9H, s).

6. N-[3(R,S)-1-tert-Butyl-2,3-dihydro-2-oxo-5-phenyl-1H-1,4-benzodiazepin-3-yl]-N'-[4-methyl-3-{(tetrazol-5-yl)amino}phenyl]urea The title compound was prepared from 3-(R,S)-amino-1-tert-butyl-1,3-dihydro-5-phenyl-2H-1,4-benzodiazepin-2-one and 4-methyl-3-[(tetrazol-5-yl)amino]aniline using a similar method to that described for Example 4; mp 193° C. (dec); δ$_H$ (360 MHz, DMSO-d$_6$) 9.25 (1H, s), 7.66–7.25 (13H, m), 6.69 (2H, s, exchanges with D$_2$O), 5.13 (1H, d, J=8.4 Hz), 1.95 (3H, s), 1.36 (9H, s); m/z (CI) 523 (M$^-$). (Found: C, 62.82; H, 5.69; N, 23.09. C$_{28}$H$_{29}$N$_9$O$_2$×0.8H$_2$O requires: C,62.51; H, 5.73; N,23.43%).

EXAMPLE 17

(−)-N-[2,3-Dihydro-5-(4-methylpiperazin-1-yl)-2-oxo-1-propyl-1H-1,4-benzodiazepin-3-yl]-N'-[3-{N-methyl-N-(tetrazol-5-yl)amino}phenyl]urea 1. Methyl 2-(N-bromoacetyl-N-propylamino) benzoate To a solution of methyl N-propylanthranilate (140 g) in dichloromethane (1l) was added bromoacetylbromide (70 ml) at room temperature. The reaction mixture was then cooled to 5° C. and a solution of sodium hydroxide (44 g) in water (850 ml) was added dropwise over 2 hours. After being stirred at room temperature for further 3 hours, the organic phase was separated, washed with 1N hydrochloric acid (1×500 ml), brine (1×500 ml), saturated sodium hydrogen carbonate (1×500 ml), dried (Na$_2$SO$_4$) and concentrated to give the title compound (209.4 g); δ$_H$ (360 MHz, CDCl$_3$) 8.00 (1H, dd, J=7.8 and 1.6 Hz), 7.67–7.62 (1H, m), 7.50 (1H, m), 7.35 (1H, dd, J=7.8 and 1.0 Hz), 3.85 (4H, m), 3.63 (1H, d, J=11.0 Hz), 3.54 (1H, d, J=11.0 Hz), 3.15 (2H, m), 1.46 (2H, m), 0.86 (3H, t, J=7.4 Hz).

2. 1-Propyl-1,2,3,4-tetrahydro-3H-1,4-benzodiazepin-2,5-dione

Ammonia gas was bubbled through an ice-cooled solution of methyl 2-(N-bromoacetyl-N-propylamino)benzoate (209 g) in methanol (2l) for 4 hours. The solution was then allowed to warm to room temperature and stirred for 16 hours before the solvent was removed under vacuum. The residue was triturated with diethyl ether to give the title compound (114 g) as a solid; $\delta_H$ (360 MHz, CDCl$_3$) 8.07 (1H, t, J=6.1 Hz), 7.88 (1H, dd, J=7.7 and 1.7 Hz), 7.58–7.56 (1H, m), 7.36–7.29 (2H, m), 4.27–4.19 (1H, m), 3.79 (2H, d, J=6.1 Hz), 3.63–3.56 (1H, m), 1.64–1.47 (2H, m), 0.82 (3H, t, J=7.4 Hz).

3. 1,2-Dihydro-5-(4-methylpiperazin-1-yl)-3H-1,4-benzodiazepin-2-one

To a solution of the product from the previous step (30 g) in anhydrous dichloromethane (400 ml) was added dropwise, over 1 hour, a solution of phosphorous pentachloride (35 g) in dichloromethane (800 ml) at room temperature. After further 1.5 hours the solvent was removed under vacuum to give 5-chloro-1,2-dihydro-1-propyl-3H-1,4-benzodiazepin-2-one hydrochloride.

To a solution of the above imino chloride (32.25 g) in dichloromethane (1l) was added a solution of N-methylpiperazine (42 ml) in dichloromethane (300 ml) over 20 minutes at room temperature, under a nitrogen atmosphere. The reaction was stirred for further 3 hours before it was washed with saturated aqueous sodium bicarbonate (1×250 ml), and brine (1×250 ml). The combined aqueous layers were re-extracted with dichloromethane (1×250 ml) and the combined organic solutions were dried (Na$_2$SO$_4$) and concentrated. The residue was dissolved in dichloromethane (300 ml) and treated with a solution of oxalic acid (25 g) in diethyl ether (200 ml). The precipitate was collected by filtration, redissolved in the minimum amount of water and basified to pH 9 with sodium hydrogen carbonate. The aqueous solution was extracted with ethyl acetate (5×200 ml) and the combined organic phases were washed with water (1×300 ml), brine (1×300 ml), then dried and concentrated to give the title compound (33 g) as solid; $\delta_H$ (360 MHz, CDCl$_3$) 7.55–7.49 (2H, m), 7.37–7.35 (1H, m), 7.28–7.24 (1H, m), 4.40–4.32 (1H, m), 3.56–3.48 (2H, m). 3.29 (4H, br s), 2.56–2.52 (2H, m), 2.33 (3H, s), 1.62–1.35 (2H, m), 0.77 (3H, t, J=7.4 Hz).

4. 1.2-Dihydro-5-(4-methylpirerazin-1-yl)-3-oximido-1-propyl-3H-1,4-benzodiazepin-2-one To a cooled (–20° C.) and stirred solution of 1,2-dihydro-5-(4-methylpiperazin-1-yl)-1-propyl-3H-1,4-benzodiazepin-2-one (28 g) in toluene (2l) was added potassium tert-butoxide (26.2 g) under a nitrogen atmosphere. The reaction mixture was stirred for 20 minutes at –20° C. before isopentyl nitrite (15 ml) was added and stirring was continued for 18 hours at this temperature. A further aliquot of potassium tert-butoxide (10.5 g) was added followed by additional isopentyl nitrite (6.3 ml) and the mixture was stirred at –20° C. for further 4 hours. After being warmed to room temperature the pH was adjusted to 7.4 by addition of 1M hydrochloric acid and the solvent was removed under vacuum. The remaining residue was purified by column chromatography on activity 3 alumina (dichloromethane-methanol-ammonia, 90:10:1) to give the title compound as a solid (16 g); mp 191°–193° C.; $\delta_H$ (360 MHz, DMSO-d$_6$) (mixture of E/Z isomers) 10.14 and 9.94 (1H, 2s), 7.62–7.26 (4H, m), 4.21 (1H, m), 3.65–3.50 (5H, m), 2.42–2.29 (4H, m), 2.19 (3H, s), 1.53–1.20 (2H, m), 0.76 (3H, m).

5. 3-Amino-1,2-dihydro-5-(4-methylpiperazin-1-yl)-1-propyl-3H-1,4-benzodiazepin-2-one Trifluoroacetate 1,2-Dihydro-5-(4-methylpiperazin-1-yl)-3-oximido-1-propyl-3H-1,4-benzodiazepin-2-one (2.0 g) was dissolved in glacial acetic acid (35 ml). Trifluoroacetic acid (4.68 ml) was added and the solution warmed to 40° C. Activated zinc powder (Fieser and Fieser, 1967, Volume 1, 1276; 3.97 g) was added and the mixture was stirred at 40° C. for 5 hours. The mixture was cooled, filtered and then evaporated to give the crude amine trifluoroacetate salt.

6. α-Amino-N-(2,3-dihydro-5-(4-methylpiperazin-1-yl)-2-oxo-1-propyl-1H-1,4-benzodiazepin-3-yl)benzene propanamide To a stirred solution of 3-amino-1,2-dihydro-5-(4-methylpiperazin-1-yl)-1-propyl-3H-1,4-benzodiazepin-2-one (2.96 g) in anhydrous dimethylformamide (30 ml) was added BOC-D-phenylalanine (2.61 g), 1-hydroxybenzotriazole (1.33 g), 1-(3-dimethylaminopropyl)-3-ethyl-carbodiimide hydrochloride (1.89 g) and triethylamine (1.37 ml). After stirring at room temperature for 15 minutes the solution was treated with saturated sodium hydrogen carbonate solution then extracted with ethyl acetate (4×100 ml). The combined organic phases were washed with saturated sodium chloride solution, dried (Na$_2$SO$_4$), evaporated to dryness and the residue purified by column chromatography on silica using 5% methanol/dichloromethane to 10% methanol/dichloromethane. The product obtained (5.28 g) was treated at 0° C. with ethyl acetate (100 ml) saturated with hydrogen chloride gas and stirred at 0° C. for 1 hour. The solution was basified to pH 9 with saturated sodium hydrogen carbonate solution, the organic layer was separated and the aqueous re-extracted with ethyl acetate (4×100 ml). The combined organic phases were dried (Na$_2$SO$_4$) and the more polar (by silica tlc) diastereomer crystallised from methanol/diethyl ether to afford a solid (460 mg. mp 152°–153° C.; Rf 0.50 in dichloromethane/methanol/ammonia (9:1:0.1) on silica plates. HPLC (Spherisorb ODS2 column, 25% acetonitrile/75% of 0.2% triethylamine in water, pH to 3 with orthophosphoric acid): R$_t$ 5.09 minutes, 99.5% pure. $\delta_H$ (360 MHz, DMSO-d$_6$) δ0.68 (3H, t, J=7 Hz), 1.20–1.29 (1H, m), 1.37–1.44 (1H, m), 2.19 (3H, s), 2.25–2.35 (2H, m), 2.40–2, 48 (2H, m), 2.59 (1H, dd, J=9 and 13 Hz), 3.00 (1H, dd, J=4 and 13 Hz), 3.10–3.30 (4H, m), 3.47 (1H, dd, J=4 and 9 Hz), 3.60–3.68 (1H, m), 4.19–4.28 (1H, m), 4.97 (1H, d, J=8 Hz), 7.16–7.30 (5H, m), 7.36–7.42 (1H, m), 7.55 (1H, d, J=8 Hz), 7.63–7.66 (2H, m), 8.76 (1H, d, J=8 Hz). (Found: C, 67.62; H, 7.24; N, 18.17. C$_{26}$H$_{34}$N$_6$O$_2$ requires 67.51; H, 7.41; N, 18.17%).

7. (–)-N-[2,3-Dihydro-5-(4-methylpiperazin-1-yl)-2-oxo-1-propyl-1H-1,4-benzodiazepin-3-yl]-N'-[3-{N-methyl-N-(tetrazol-5-yl)amino}phenyl]urea Phenyl isothiocyanate (117 µl) was added to a stirred solution of the foregoing diastereomeric amide (0.41 g) in anhydrous dichloromethane (20 ml) then heated at 40° C. for 3 hours. The reaction mixture was evaporated and the residue purified by column chromatography on silica using dichloromethane to dichloromethane/methanol/ammonia (20:1:0.1), gradient elution, to afford the thiourea (0.53 g). Trifluoroacetic acid (20 ml) was added and the mixture was stirred at room temperature for 40 minutes. The mixture was evaporated to dryness, the residue dissolved in water (50 ml), washed with diethyl ether (20 ml) then the aqueous was freeze dried and azeotroped with toluene to afford the homochiral amine trifluoroacetate (0.54 g) which was used crude.

To a cooled (0° C.) and stirred solution of 3-[(N-methyl-N-(tetrazol-5-yl)amino]aniline (138 mg) in anhydrous tetrahydrofuran (10 ml) was added solid triphosgene (70.9 mg). After 5 minutes of stirring, anhydrous triethylamine (302 µl) (pH 8) was added dropwise and the mixture was allowed to warm to room temperature and stirred for 20 minutes. After being cooled to 0° C., a solution of the foregoing homochiral amine trifluoroacetate salt (260 mg) in anhydrous tetrahydrofuran was added followed by additional anhydrous triethylamine until the solution reached pH 8. The reaction mixture was then allowed to warm to room temperature, stirred for 1 hour then poured into water. Solvents were removed and the residue was purified by preparative HPLC ($C_{18}$ DYNAMAX-300A, 18% acetonitrite-0.1% trifluoroacetic acid in water) to give the title compound as a solid; mp 141°–142° C.; $\delta_H$ (360 MHz, $D_2O$) 7.9–7.6 (3H, m), 7.67 (1H, m), 7.50 (1H, s), 7.40 (1H, m), 7.15 (1H, d, J=6.5 Hz), 7.01 (1H, d, J=6.5 Hz), 5.24 (1H, s), 4.3–3.4 (10H, m), 3.39 (3H, s), 3.00 (3H, s), 1.63–1.45 (2H, m), 0.73 (3H, t, J=7.0 Hz); m/z (FAB) 532 ($M^+$+1). (Found: C, 45.83; H, 4.78; N, 19.91. $C_{26}H_{33}N_{11}O_2 \times 2$ $CF_3CO_2H \times 1.2H_2O$ requires: C, 46.12; H, 4.83; N, 19.78%).

EXAMPLE 18

N-[3(R,S)-5-Cyclohexyl-2,3-dihydro-2-oxo-1-propyl-1H-1,4-benzodiazepin-3-yl]N'-[3-[(1H-imidazol-2-ylamino)methyl]phenyl]urea 1 : 5-Cyclohexyl-1,3-dihydro-1-propyl-3(R,S)-[(benzyloxy-carbonyl)amino]-2H-1,4-benzodiazepin-2-one A solution of 5-cyclohexyl-1,3-dihydro-3(R,S)-[(benzyloxycarbonyl)amino]-2H-1,4-benzodiazepin-2-one (Intemediate 1, step 2, 2 g) in anhydrous dimethylfomamide (15 ml), under an atmosphere of nitrogen, was treated with sodium hydride (0.22 g of a 55–60% dispersion in mineral oil), at 0° C. After 45 min at 0° C., 1-iodopropane (0.55 ml) was added in one portion and the solution allowed to reach ambient temperature and stirred overnight. After this time the solvent was removed under reduced pressure, and the crude residue partitioned between water (25 ml) and dichloromethane (25 ml). The organic phase was separated and the aqueous phase extracted with dichloromethane (3×25 ml). The combined organic layers were washed with brine (50 ml), dried ($MgSO_4$) and evaporated in vacuo. The residue was triturated with diethyl ether to give the title compound (1.74 g) as a solid. mp 160°–163° C.; $^1H$ NMR (360 MHz, $CDCl_3$)δ0.82 (3H, t, J=10.5 Hz), 0.94–1.48 (5H, m), 1.50–1.76 (5H, m), 1.79–1.90 (1H, m), 1.96–2.08 (1H, m), 2.70–2.84 (1H, m), 3.46–3.59 (1H, m), 4.22–4.35 (1H, m), 5.06–5.16 (3H, m), 5.07 (1H, d, J=12.0 Hz), 7.21–7.40 (7H, m), 7.44–7.59 (2H, m).

2 : 5-Cyclohexyl-1,3-dihydro-1-propyl-3(R,S)-[(4-nitrophenyloxycarbonyl)amino]-2H-1,4-benzodiazepin-2-one The product of step 1 (1.6 g) was dissolved in formic acid/methanol (130 ml of a 4.5% (v/v) solution), and added over 5 min to a stirred suspension of 10% palladium on carbon (0.4 g, 25% (w/w)) in formic acid/methanol (20 ml of a 4.5% (v/v) solution). After 1 h at ambient temperature, the catalyst was filtered off and washed sequentially with methanol and acetone. The filtrate was evaporated in vacuo and the residue partitioned between ethyl acetate (25 ml) and 10% sodium carbonate solution (25 ml). The organic phase was separated and the aqueous phase extracted with ethyl acetate (3×25 ml). The combined organic phases were dried ($Na_2SO_4$) and evaporated in vacuo to give a yellow gum which was used without further purification.

A solution of the crude amine (1.1 g) in anhydrous tetrahydrofuran (15 ml) under an atmosphere of nitrogen, at 0° C., was treated with triethylamine (0.51 ml), followed by a solution of 4-nitrophenyl chloroformate (0.74 g) in anhydrous tetrahydrofuran (15 ml) dropwise. After stirring at ambient temperature for 15 min, the solid which precipitated from the mixture was removed by filtration, and the filtrate was evaporated in vacuo to leave an orange solid. The solid was triturated with diethyl ether to give the title compound (1.3 g); mp 152°–155° C.; $^1H$ NMR (360 MHz, $CDCl_3$) δ0.85 (3H, t, J=7.4 Hz), 1.02–1.50 (6H, m), 1.56–1.76 (4H, m), 1.84–1.93 (1H, m), 2.00–2.08 (1H, m), 2.76–2,87 (1H, m), 3.53–3.63 (1H, m), 4.26–4.36 (1H, m), 5.14 (1H, d, J=8.0 Hz), 6.93 (1H, d, J=8.3 Hz), 7.22–7.40 (4H, m), 7.50–7.62 (2H, m), 8.18–8.26 (2H, m).

3 : 3-[(1H-Imidazol-2-ylamino)-methyl]-1-nitro benzene

A solution of sodium carbonate (4.01 g) in water (40 ml) was added to 2-aminoimidazole sulphate (10 g) and the mixture stirred for 10 min. The solvent was evaporated in vacuo and the residue suspended in ethanol. The resulting precipitate was removed by filtration and the filtrate evaporated to leave the crude 2-aminoimidazole, as a brown oil.

The oil was taken up in ethanol (180 ml) and 3-nitrobenzaldehyde (11.44 g) followed by acetic acid (4.3 ml) was added to the solution. After stirring at room temperature for 30 min the mixture was heated at reflux, under nitrogen, for 4 h. The solvent was evaporated in vacuo and the residue suspended in ethanol (300 ml) and treated with sodium borohydride (9.08 g) portionwise, over a period of 30 min. The mixture was then stirred at room temperature for 16 h. The solvent was removed in vacuo and the residue partitioned between water (100 ml) and ethyl acetate (200 ml). The aqueous phase was separated and the organic layer extracted with 1M hydrochloric acid (3×100 ml). The combined acidic layers were basified using 5M sodium hydroxide solution and then extracted with dichloromethane (3×100 ml). The combined organic layers were dried ($Na_2SO_4$) and evaporated in vacuo. The residue was chromatographed on silical gel, using dichloromethane:methanol:ammonia (95:5:1) as the eluant, to afford a gum (3 g), which was triturated with ether to give the title compound (1.73 g) as a brown solid. $^1H$ NMR (360 MHz, $D_6$-DMSO) δ 4.44 (2H, d, J=6.3 Hz), 6.33 (1H, t, J=6.4 Hz), 6.45 (2H, brs), 7.60 (1H, t, J=7.9 Hz), 7.78 (1H, d, J=7.4 Hz), 8.07 (1H, d, J=7.9 Hz), 8.21 (1H, s), 10.41 (1H, brs). MS (CI, $NH_3$) 218 ($M^+$).

4 : 3-[(1-tert-Butyloxycarbonyl)-imidazol-2-ylamino)methyl]-1-nitrobenzene

To a suspension of the product of step 3 (200 mg) in anhydrous dichloromethane (20 ml) was added a solution of di-tert-butyl dicarbonate (0.24 g) in anhydrous dichloromethane (5 ml) dropwise. The mixture was stirred at room temperature for 2 h, then washed with water (20 ml). The organic layer was dried ($Na_2SO_4$) and evaporated in vacuo. The residue was chromatographed on silica gel using petrol (66/80):ethyl acetate (1:1) as the eluant to yield the title compound (256 mg) as a solid; $^1H$ NMR (360 MHz, $CDCl_3$)δ1.6 (9H, s), 4.73 (2H, d, J=6.1 Hz), 6.56 (1H, d, J=2.0 Hz), 6.64 (1H, d, J=2.0 Hz), 6.99 (1H, brs), 7.50 (1H, t, J=7.9 Hz), 7.73 (1H, d, J=8.2 Hz), 8.12 (1H, d, J=8.3 Hz), 8.24 (1H, s). MS (CI, $NH_3$) 318 ($M^+$).

5 : 1-Amino-3-[(1-tert-butyloxycarbonyl)-imidazol-2-ylamino)methyl]-benzene

To a solution of the product of step 4 (250 mg) in ethanol (20 ml) was added palladium on carbon catalyst (150 mg, 60% (w/w)) as a slurry in water (2 ml). The mixture was hydrogenated at 40 psi for 2 min then the catalyst was removed by filtration and the solvent evaporated in vacuo. The residue was chromatographed on silica gel, using dichloromethane:methanol (95:5) as the eluant, to give the aniline (210 mg) as a solid; $^1H$ NMR (360 MHz, $CDCl_3$) δ1.57 (9H, s), 3.68 (2H, brs), 4.52 (2H, d, J=5.6 Hz), 6.58 (1H, d, J=1.9 Hz), 6.59–6.61 (1H, m), 6.72–6.80 (3H, m), 6.81 (1H, d, J=1.9 Hz), 7.12 (1H, t, J=7.8 Hz). MS (CI, $NH_3$) 289 (M+1).

6: N-[3(R,S)-5-Cyclohexyl-2,3-dihydro-2-oxo-1-propyl-1H-1,4-benzodiazepin-3-yl]N'-[3-[(1H-imidazol-2-ylamino)methyl]phenyl]urea To a solution of the product of step 2 (150 mg) in anhydrous dimethylformamide (3 ml) at room temperature, under nitrogen, was added triethylamine (45 µl). The solution was stirred for 5 min before a solution of the product of step 5 (102 mg) in anhydrous dimethylformamide (1.5 ml) was added.

The solution was then heated at 50° C. for 5 h under nitrogen. After cooling the solvent was evaporated in vacuo and the residue partitioned between ethyl acetate (20 ml) and 10% sodium carbonate solution (4×20 ml). The organic layer was then washed with water (20 ml), dried ($Na_2SO_4$) and evaporated to afford a gum which was triturated with ether and the resulting precipitate collected by filtration. The solid was chromatographed on silica gel using a gradient elution of dichloromethane:methanol (95:5) followed by dichloromethane:methanol:ammonia (90:10:1) and finally methanol. The title compound (90 mg) was isolated as a solid; $^1H$ NMR (360 MHz, $D_6$-DMSO)δ0.73 (3H, t, J=7.3 Hz), 0.88–1.02 (1H, m), 1.07–1.56 (7H, m), 1.58–1.69 (2H, m), 1.74–1.84 (1H, m), 1.87–1.97 (1H, m), 2.90–3.01 (1H, m), 3.61–3.72 (1H, m), 4.16–4.28 (3H, m), 5.03 (1H, d, J=7.9 Hz), 5.99–6.04 (1H, m), 6.44 (2H, s), 6.88 (1H, d, J=7.6 Hz), 7.13 (1H, t, J=7.8 Hz), 7.22–7.30 (3H, m), 7.34–7.41 (1H, m), 7.60–7.66 (2H, m), 7.76 (1H, d, J=7.9 Hz), 8.95 (1H, s). MS (CI, $NH_3$) 513 ($M^+$).

EXAMPLE 19

N-[3(R,S)-5-Cyclohexyl-2,3-dihydro-2-oxo-1-propyl-1H-1,4-benzodiazepin-3-yl]N'-[3-[(1H-imidazol-2-yl)amino]phenyl]urea 1: 3-Nitrophenyl thiourea To a cooled (0° C.) and stirred solution of 1-amino-3-nitrobenzene (10 g) in anhydrous tetrahydrofuran (500 ml), under nitrogen, was added thiophosgene (5.6 ml) dropwise. After 5 min triethylamine (29 ml) was added dropwise and the mixture stirred for a further 5 min at 0° C. then at room temperature for 10 min. The mixture was then re-cooled to 0° C. and ammonia gas bubbled through the mixture for 15 min. The resultant solid was removed by filtration and the filtrate evaporated in vacuo to afford a gum which was triturated with ethyl acetate to give the thiourea (7.3 g) as a solid. $^1H$ NMR (250 MHz, $D_6$-DMSO)δ7.59 (1H, dd, J=8.2 and 8.2 Hz), 7.83 (1H, m), 7.92 (1H, m), 8.64 (1H, m), 10.09 (1H, brs). MS (CI, $NH_3$) 197 ($M^+$).

2: S-Methyl-3-nitronphenylisothiouronium iodide

To a stirred suspension of 3-nitrophenyl thiourea (6.83 g) in ethanol (60 ml) at 0° C. under nitrogen, was added methyl iodide (2.48 ml) dropwise. After addition the cooling bath was removed and the mixture heated at reflux for 1 h. The mixture was allowed to cool to ambient temperature then the solvent evaporated to afford a solid which was triturated with ethyl acetate to afford the title compound (10.99 g) as a solid. $^1H$ NMR (360 MHz, $D_6$-DMSO)δ2.72 (3H, s), 7.78–7.84 (2H, m), 8.24–8.27 (2H, m), 9.20–10.00 (1H, brs). MS (CI, $NH_3$) 211 ($M^+$).

3 : 2-(3-Nitrophenyl)aminoimidazole

To a stirred suspension of the product of step 2 (5.8 g) in ethanol (20 ml) at 0° C., under nitrogen, was added 2-aminoacetaldehyde diethyl acetal (3.5 ml) dropwise. After addition the cooling bath was removed and the reactiom mixture heated at reflux for 3 h. After this time more 2-aminoacetaldehyde diethyl acetal (0.4 ml) was added and the mixture heated for a further 1 h. More 2-aminoacetaldehyde diethyl acetal (0.4 ml) was then added and the mixture heated at reflux for a further 1 h. The mixture was cooled to room temperature then evaporated in vacuo. The residue was partitioned between ethyl acetate (50 ml) and water (50 ml). The aqueous phase was separated and the organic phase washed with water (50 ml). The organic layer was separated and dried ($Na_2SO_4$). The aqueous phase was basified to pH 14 using 10% aqueous sodium hydroxide solution then extracted with dichloromethane (3×50 ml). The combined organic layers were dried ($Na_2SO_4$). The dried ethyl acetate and dichloromethane layers were combined and evaporated to afford crude 1-(3-nitrophenyl)-3-(β-β-diethoxyethyl)guanidinium iodide as an oil which was used without further purification.

The crude guanidinium salt was dissolved in concentrated hydrochloric acid (20 ml) and iso-propanol (5 ml). The solution was heated at 50° C. for 15 min then allowed to cool to ambient temperature and then washed with diethyl ether (2×20 ml). The aqueous phase was separated, basified to pH 14 using sodium hydroxide pellets, and partitioned with dichloromethane (100 ml). Activated charcoal was added to the mixture, and, after filtration, the organic layer was separated. The aqueous phase was extracted with more dichloromethane (2×50 ml), then the combined organic extracts were washed with water (20 ml). The organic layer was separated, treated with activated charcoal and filtered. The filtrate was dried ($Na_2SO_4$), evaporated and the residue chromatographed on silica gel, using a gradient elution of ethyl acetate followed by dichloromethane:methanol (90:10). The title compound (500 mg) (Rf 0.5, ethyl acetate) was isolated as an orange solid. $^1H$ NMR (360 MHz, $CDCl_3$+$D_6$-DMSO)δ6.77 (2H, s), 7.38 (1H, dd, J=8.2 and 8.2 Hz), 7.65 (1H, dd, J=7.6 and 1.7 Hz), 7.83 (1H, dd, J=7.7 and 1.5 Hz), 8.30 (1H, t, J=2.2 Hz), 8.40–9.00 (1H, brs). MS (CI, $NH_3$) 204 ($M^+$).

4 : 1-(tert-Butyloxycarbonyl)-2-(3-nitrophenyl) amino imidazole

To a stirred solution of 2-(3-nitrophenyl)aminoimidazole (412 mg) in anhydrous dichloromethane (5 ml) and anhydrous tetrahydrofuran (3 ml), under nitrogen, was added a solution of di-tert-butyl dicarbonate (528 mg) in dry tetrahydrofuran (2 ml). The solution was stirred at room temperature for 4 h whereupon more of a solution of di-tert-butyl dicarbonate (118 mg) in anhydrous tetrahydrofuran (2 ml) was added. The solution was stirred for 2 days then diluted with dichloromethane (20 ml) and washed with water (20 ml). The organic phase was separated, dried ($Na_2SO_4$) and evaporated in vacuo. The residue was chromatographed on silica gel, using petrol (60/80):ethyl acetate (6:1) as the eluant to yield the title compound (611 mg) as a solid. $^1H$ NMR (360 MHz, $CDCl_3$) δ1.65 (9H, s), 6.76 (1H, d, J=1.9 Hz), 6.97 (1H, d, J=1.9 Hz), 7.47 (1H, t, J=8.1 Hz), 7.84 (1H, dd, J=8.1 and 1.8 Hz), 8.03 (1H, dd, J=8.1 and 1.9 Hz), 8.64 (1H, t, J=1.8 Hz), 9.36 (1H, brs). MS (CI, $NH_3$) 304 ($M^+$).

5 : 2-(3-Aminophenyl)amino-1-(tert-butyloxycarbonyl) imidazole

A solution of the product of step 4 (305 mg) in ethanol (40 ml), containing palladium on carbon catalyst (120 mg, 39% (w/w)), was hydrogenated at 25 psi for 15 min. After this time the catalyst was filtered off and washed with ethanol and dichloromethane. The filtrate was evaporated in vacuo and the residue chromatographed on silica gel, using petrol (60/80):ethyl acetate (2:1) as the eluant. The aniline (205 mg) was isolated as a solid. $^1H$ NMR (360 MHz, $CDCl_3$) δ1.63 (9H, s), 3.57 (2H, brs), 6.35 (1H, dd, J=7.9 and 2 Hz), 6.71 (1H, d, J=1.9 Hz), 6.80 (1H, dd, J=7.9 and 2 Hz), 6.91 (1H, d, J=1.9 Hz), 7.07 (1H, t, J=7.9 Hz), 7.30 (1H, t, J=2.1 Hz), 9.02 (1H, brs). MS (CI, $NH_3$) 275 (M+1).

6: N-[3(R,S)-5-Cyclohexyl-2,3-dihydro-2-oxo-1-propyl-1H-benzodiazepin-3-yl]N'-[3-[(1-(tert-butyloxycarbonyl) imidazol-2-yl]amino)phenyl]urea To a stirred solution of 5cyclohexyl-1,3-dihydro-1-propyl-3(R,S)-[(4-nitrophenyloxycarbonyl)amino]-2H-1,4-benzodiazepin-2-one (220 mg) [Example 18, Step 2] in anhydrous dimethylformamide (4 ml) at room temperature, under nitrogen, was added triethylamine (66 µl) dropwise. After stirring at room temperature for 5 min a solution of the product of step 5 (143 mg) in anhydrous dimethylformamide (4 ml) was added dropwise and the solution heated at 50° C. for 4 h. After this time more triethylamine (15 µl) was added and the mixture heated at 50° C. for a further 1.5 h. More triethylamine (20 µl) was then added and the solution heated for a further 1.5 h.

The solvent was evaporated in vacuo and the residue partitioned between ethyl acetate (20 ml) and water (20 ml). The aqueous phase was separated and the organic layer washed with 10% sodium carbonate solution (2×20 ml) followed by water (20 ml). The organic phase was separated, dried ($Na_2SO_4$) and evaporated in vacuo. The residue was chromatographed on silica gel, using petrol (60/80):ethyl acetate (2:1) as the eluant, to afford the title compound (82 mg) as a solid. $^1$H NMR (360 MHz, $CDCl_3$) δ 0.81 (3H, t, J=7.4 Hz), 1.04–1.72 (19H, m), 1.82–1.87 (1H, m), 2.01–2,06 (1H, m), 2.75–2,82 (1H, m), 3.50–3.58 (1H, m), 4.26–4.34 (1H, m), 5.31 (1H, d, J=7.9 Hz), 6.69 (1H, brs), 6.77 (1H, d, J=7.7 Hz), 6.89 (1H, d, J=2.0 Hz), 7.02 (1H, d, J=8.0 Hz), 7.15–7.28 (4H, m), 7.34 (1H, d, J=8.1 Hz), 7.47 (1H, dd, J=7.1 and 7.1 Hz), 7.55 (1H, d, J=6.8 Hz), 7.68 (1H, brs), 9.05 (1H, brs), MS (CI, $NH_3$) 600 (M+1).

7: N-[3(R,S)-5-Cyclohexyl-2,3-dihydro-2-oxo-1-propyl-1H-1,4-benzodiazepin-3-yl]N'-[3-[(1-(H)imidazol-2-yl)amino]phenyl]urea To a solution of the product of step 6 (70 mg) in anydrous dichloromethane (5 ml) at room temperature, under nitrogen, was added trifluoroacetic acid (0.5 ml). The solution was stirred for 3 h then the solvent removed in vacuo and the residue azeotroped with toluene (10 ml). The residue was partitioned between dichloromethane (20 ml) and 10% sodium hydroxide solution (20 ml). The organic phase was separated, dried ($Na_2SO_4$) and evaporated. The residue was chromatographed on silica gel, using dichloromethane:methanol (93:7) as the eluant. The title compound (35 mg) was isolated as a solid. $^1$H NMR (360 MHz, $D_6$-DMSO)δ0.73 (3H, t, J=7.4 Hz), 0.90–1.52 (8H, m), 1.60–1.64 (2H, m), 1.74–1.78 (1H, m), 1.90–1.94 (1H, m), 2.92–2,96 (1H, m), 3.62–3.69 (1H, m), 4.16–4.25 (1H, m), 5.02 (1H, d, J=8.5 Hz), 6.60–6.71 (2H, m), 6.82 (1H, d, J=7.9 Hz), 6.89 (1H, m), 6.99 (1H, dd, J=8.0 and 8.0 Hz), 7.23 (1H, d, J=8.5 Hz), 7.35–7.40 (2H, m), 7.61–7.63 (2H, m), 7.76 (1H, d, J=7.9 Hz), 8.47 (1H, s), 8.90 (1H, s), 10.87 (1H, brs). MS (FAB) 500 (M+1).

EXAMPLE 20

N-[3(R,S)-5-Cycloheptyl-2,3-dihydro-1-methyl-2-oxo-1H-1,4-benzodiazepin-3-yl]N'-[3-[(1H-imidazol-2-ylamino)methyl]phenyl]urea 1 : 2-Aminophenylcycloheptylmethanone Over a period of 1 h a solution of cycloheptyl bromide (37.8 g) in diethyl ether (200 ml) was added dropwise to a slurry of magnesium turnings (5.28 g) and a crystal of iodine in diethyl ether (20 ml) at reflux. The mixture was stirred for a further hour whereupon the Grignard solution was cannulated into a pressure equalising dropping funnel, attached to a three-necked round-bottomed flask, which was trader an atmosphere of nitrogen.

A solution of 2-aminobenzonitrile (8.26 g) in diethyl ether (200 ml), at 0° C., was treated dropwise with the Grignard reagent prepared above, over a period of 30 min. Once the addition was complete, the mixture was warmed to room temperature and stirred for 16 h under nitrogen. The solution was cooled to 0° C., quenched with 5N hydrochloric acid (45 ml), and basified using solid sodium hydroxide (8.9 g). The aqueous solution was extracted with ethyl acetate (2×100 ml) and the combined organic layers were dried ($Na_2SO_4$) and evaporated. The residue was chromatographed on silica gel using 2:1 petrol:ethyl acetate as the eluant. This gave the title compound (8.2 g) as an oil. $^1$H NMR (250 MHz, $CDCl_3$)δ1.40–2,10 (12H, m), 3.34–3.50 (1H, m), 6.30 (2H, brs), 6.60–6.70 (2H, m), 7.20–7.30 (1H, m), 7.70–7.80 (1H, m). TLC (silica, petrol (60/80):ethyl acetate 2:1). Rf=0.50.

2: Cycloheptyl-2-(a-(benzyloxycarbonylamino)-α-isopropylthioacetylamino)phenyl methanone α-(iso-Propylthio)-N-(benzyloxycarbonyl)glycine (21.9 g) was dissolved in dichloromethane (450 ml) and cooled to 0° C. The stirred solution was then treated with triethylamine (21.5 ml) bis(2-oxo-3-oxazolidinyl)phosphinic chloride (19.7 g) and 2-aminophenyl cycloheptyl methanone (12.0 g). The mixture was warmed to ambient temperature and stirred for 2 h. The mixture was then washed in succession with 10% citric acid solution (100 ml), water (100 ml), saturated sodium bicarbonate solution (100 ml) and brine (100 ml). The dried ($Na_2SO_4$) organic phase was evaporated and the residue chromatographed on silica gel using 8:1 petrol:ethyl acetate as eluant. This afforded the title compound as a solid (13.5 g). $^1$H NMR (250 MHz, $CDCl_3$)δ1.10–2.00 (18, m), 3.14–3.34 (1H, m), 3.40–3.56 (1H, m), 5.16–5.22 (2H, m), 5.56 (1H, d, J=5 Hz), 5.98 (1H, d, J=5 Hz), 7.10–7.18 (1H, m), 7.24–7.44 (5H, m), 7.50–7.60 (1H, m), 7.84–7.94 (1H, m), 8.60–8.70 (1H, m), 12.28 (1H, brs). TLC (silica, petrol (60/80):ethyl acetate 3:1). Rf=0.45.

3 : 3(R,S)-[(Benzyloxycarbonyl)amino]-5-cycloheptyl-1,3-dihydro-2H-1,4-benzodiazepin-2-one The product of step 2 (10 g) was dissolved in anhydrous tetrahydrofuran (500 ml) and cooled to 0° C. Ammonia gas was bubbled through the stirred solution for 10 min before adding mercuric chloride (8.5 g) in one portion. Ammonia was continually bubbled through the solution for a further hour, then the suspended solids were filtered off. The solvent was evaporated in vacuo to leave an oil, which was used without further purification.

The crude α-aminoglycinamide was dissolved in glacial acetic acid (200 ml) and treated with ammonium acetate (7.7 g). The resulting reaction mixture was stirred at room temperature overnight, before removing the solvent in vacuo. The residue was partitioned between ethyl acetate (300 ml) and 10% sodium hydroxide solution (200 ml). The dried ($Na_2SO_4$) organic layer was evaporated and the residue chromatographed on silica gel with 2:1 petrol:ethyl acetate as eluant. This afforded the title product (8.0 g) as a solid. $^1$H NMR (250 MHz, $CDCl_3$) δ 1.18–2,20 (12H, m), 2.90–3.07 (1H, m), 5.06–5.24 (3H, m), 6.46 (1H, d, J=10 Hz), 7.04–7.12 (1H, m), 7.22–7.42 (6H, m), 7.44–7.56 (1H, m), 7.58–7.68 (1H, m), 10.30 (1H, brs). TLC (silica, petrol (60/80):ethyl acetate 2:1). Rf=0.15.

4: 3(R,S)-[(Benzyloxycarbonyl)amino]-5-cycloheptyl-1,3-dihydro-1-methyl-2H-1,4-benzodiazepin-2-one The product of step 3 (500 mg) in anhydrous toluene (40 ml) was heated to reflux. A solution of dimethylformamide dimethyl acetal (7861 µl) in anhydrous toluene (10 ml) was added dropwise and the mixture was heated at reflux for a further hour. The solvent was evaporated and the residue triturated with diethyl ether to afford the title compound (441 mg) as a solid. $^1$H NMR (360 MHz, $CDCl_3$)δ1.24–1.90

(11H, m), 2.00–2.14 (1H, m), 2.90–3.00 (1H, m), 3.40 (3H, s), 5.04–5.18 (3H, m), 6.52 (1H, d, J=7.5 Hz), 7.24–7.60 (9H, m). TLC (silica, petrol (60/80): ethyl acetate 2:1). Rf=0.30.

5 : 5-Cycloheptyl-1,3-dihydro-1-methyl-3(R,S)-[(4-nitrophenyloxycarbonyl)amino-2H-1,4-benzodiazepin-2-one The product of step 4 (0.67 g) was dissolved in hydrobromic acid (4 ml of a 30% solution in glacial acetic acid) and stirred at room temperature for 20 min. The solution was then added dropwise to anhydrous diethyl ether (20 ml) at 0° C. and the resultant solid filtered off and washed with ether. The solid was partitioned between dichloromethane (50 ml) and 10% sodium hydroxide solution (50 ml). The organic layer was separated, dried ($Na_2SO_4$) and evaporated in vacuo to afford crude 3(R,S)-amino-5-cycloheptyl-1,3-dihydro-1-methyl-2H-1,4-benzodiazepin-2-one as a viscous oil.

The amine was dissolved in anhydrous tetrahydrofuran (9 ml) under an atmosphere of nitrogen, at room temperature, and triethylamine (221 μl) was added dropwise. A solution of 4-nitrophenyl chloroformate (322 mg) in anhydrous tetrahydrofuran (9 ml) was then added, and the reaction mixture stirred for a further 3 h. After this time the undissolved solid was filtered off, washed with tetrahydrofuran, and the filtrate evaporated in vacuo. The residue was azeotroped with toluene (2×50 ml) then triturated with anhydrous ether to afford the title compound (425 mg as a solid. TLC (silica, petrol (60/80):ethyl acetate 2:1). Rf=0.3. $^1$H NMR (360 MHz, $CDCl_3$) δ 1.22–2.10 (12H, m), 2.98 (1H, m), 3.45 (3H, s), 5.15 (1H, d, J=8.2 Hz), 6.89 (1H, d, J=9.2 Hz), 7.26–7.35 (4H, m), 7.49–7.60 (2H, m), 8.22 (2H, d, J=7.1 Hz).

6: N-[3(R,S)-5-Cycloheptyl-2,3-dihydro-1-methyl-2-oxo-1H-1,4-benzodiazepin-3-yl]N'-[3-[(1H-imidazol-2-ylamino)methyl]phenyl]urea To a solution of the product of step 5 (169 mg) in anhydrous dimethylformamide at room temperature, under nitrogen, was added triethylamine (51 μl). The solution was stirred for 5 min then a solution of 1-amino-3-[(1-(tert-butyloxycarbonyl)-imidazol-2-ylamino)methyl]benzene (Example 18, step 5 117 mg) in anydrous dimethylformamide (2 ml) was added dropwise. The solution was heated at 50° C. for 3 h then the solvent was evaporated in vacuo, and the residue partitioned between ethyl acetate (25 ml) and 10% sodium carbonate solution (4×25 ml). The organic layer was separated, washed with water (20 ml) then dried ($Na_2SO_4$). The solvent was evaporated in vacuo and the residue triturated with anhydrous ether (20 ml) to afford N-[3(R,S)-5-cycloheptyl-2,3-dihydro-1-methyl-2-oxo-1H-1,4-benzodiazepin-3-yl]N'-[3-[(1-(tert-butyloxycarbonyl)imidazol-2-ylamino]methyl)phenyl]urea (74 mg) as a colourless solid, which was used without further purification.

To a solution of N-[3(R,S)-5-cycloheptyl-2,3-dihydro-1-methyl-2-oxo-1H-1,4-benzodiazepin-3-yl]N'-[3-[(1-(tert-butyloxycarbonyl)imidazol-2-ylamino]methyl)phenyl] urea in anhydrous dichloromethane (5 ml) at room temperature, under nitrogen, was added trifluoroacetic acid (0.5 ml). After stirring for 3 h the solvent was evaporated in vacuo and the residue azeotroped with toluene (20 ml). The residue was partitioned between ethyl acetate (20 ml) and water (20 ml). The organic layer was separated, washed with 0.5M sodium carbonate solution (2×20 ml) and water (20 ml), then the organic layer separated and dried ($Na_2SO_4$). The solvent was evaporated and the residue chromatographed on silica gel using a gradient elution of dichloromethane:methanol (90:10) followed by methanol to afford the title compound (33 mg) as a white solid. $^1$H NMR (360 MHz, $D_6$-DMSO) δ 1.12–1.80 (11H, m), 1.92–1.97 (1H, m), 3.10–3.18 (1H, m), 3.32 (3H, s), 4.25 (2H, d, J=6.2 Hz), 5.04 (1H, d, J=8.4 Hz) 6.42 (1H, m), 6.49 (2H, s), 6.87 (1H, d, J=7.6 Hz), 7.14 (1H, t, J=7.9 Hz), 7.23–7.29 (3H, m), 7.37 (1H, dd, J=7.2 and 7.2 Hz), 7.54 (1H, m), 7.63 (1H, dd, J=7.1 and 7.1 Hz), 7.76 (1H, d, J=6.7 Hz), 8.95 (1H, s). MS (FAB) 500 (M+1).

EXAMPLE 21A

Tablets Containing 1–25 mg of Compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 21B

Tablets Containing 26–100 mg of Compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 22

Parenteral Injection

|  | Amount mg |
| --- | --- |
| Compound of formula (I) | 1 to 100 |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a protion of the water. The compound of formula (I) is dissolved or suspended in the solution and made up to volume.

EXAMPLE 23

Topical Formulation

|  | Amount mg |
| --- | --- |
| Compound of formula (I) | 1–10 |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

Biological Activity

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM N-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20 mM (HEPES)), 1 mM ethylene glycol-bis-(β-aminoethylether-N,N'-tetraacetic acid) (EGTA), 5 mM MgCl$_2$, 150 mM NaCl, bacitracin 0.25 mg/ml, soya bean trypsin inhibitor 0.1 mg/ml, and bovine serum albumin 2 mg/ml pH 6.5 at 25° C.) using a Teflon (trademark) homogenizer, 15 strokes at 500 rpm. The homogenate was further diluted in binding assay buffer to give a final concentration of 0.5 mg original wet weight/1 ml buffer. For the binding assay, 50 µl of buffer (for total binding) or unlabelled CCK-8 sulphated to give a final concentration of 1 µM (for nonspecific binding) or the compounds of Formula I (for determination of inhibition of $^{125}$I-CCK-8 binding) and 50 µl of 500 pM $^{125}$I-CCK-8 (i.e. 50 pM final concentration) were added to 400 µl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The P$_2$ pellet was resuspended in binding assay buffer (20mM HEPES, 5 mM MgCl$_2$, 0.25 mg/ml bacitracin, 1 mM EGTA pH 6.5 at 25° C.), using a Teflon (trademark) homogenizer (5 strokes at 500 rpm) to give a final concentration of 10 mg original wet weight/1.2 ml buffer. For the binding assay, 50 µl of buffer (for total binding) or unlabelled CCK-8 sulphated to give a final concentration of 1 µM (for nonspecific binding) or the compounds of Formula I (for determination of inhibition of $^{125}$I-CCK-8 binding) and 50 µl of 500 pM $^{125}$I-CCK-8 (i.e. final concentration of 50 pM) were added to 400 µl of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

In Vitro Results Effects of the Compounds of Formula I on $^{125}$I-CCK-8 Receptor Binding The preferred compounds of Formula I are those which produced dose-dependent inhibition of specific $^{125}$I-CCK-8 binding as defined as the difference between total and non-specific (i.e. in the presence of 1 µM CCK) binding.

Drug displacement studies were performed with at least 10 concentrations of compounds of Formula I and the IC$_{50}$ values were determined by regression analysis IC$_{50}$ refers to the concentration of the compound required to inhibit 50% of specific binding of $^{125}$I-CCK-8.

The data in Table I were obtained for compounds of Formula I.

TABLE I

| CCK RECEPTOR BINDING RESULTS IC$_{50}$ (nM) | | |
| --- | --- | --- |
| Compound of Ex # | $^{125}$I-CCK Pancreas | $^{125}$I-CCK Brain |
| 1 | 9.5 | 0.82 |
| 2 | 6.5 | 0.31 |
| 3 | 10 | 0.11 |
| 4 | 400 | 0.10 |
| 5 | 200 | 0.70 |
| 6 | 153 | 0.284 |
| 7 | >3000 | 0.575 |
| 8 | >3000 | 5.7 |
| 9 | >3000 | 7.4 |
| 10 | 802 | 0.042 |
| 11 | 600 | 0.30 |
| 12 | >3000 | 1.09 |
| 13 | >3000 | 20.4 |
| 14 | 4080 | 0.11 |
| 15 | 42.8 | 1300 |
| 16 | 3610 | 497 |
| 17 | >3000 | 0.93 |
| 18 | 109 | 14.0 |
| 19 | 1.33 | 82.9 |
| 20 | 84.5 | 33.9 |

We claim:

1. A compound of formula (I), or a pharmaceutically acceptable salt thereof:

(I)

wherein:

$R^1$ represents $(CH_2)_q$imidazolyl, $(CH_2)_q$tetrazolyl, $(CH_2)_q$triazolyl, (where q is 1, 2 or 3); $C_{1-6}$alkyl optionally substituted by one or more groups selected from halo, hydroxy and $NR^6R^7$ (where $R^6$ and $R^7$ each independently represents H or $C_{1-4}$alkyl, or $R^6$ and $R^7$ together form a chain $(CH_2)_p$ where p is 4 or 5); $C_{3-7}$cycloalkyl; cyclopropylmethyl; $CH_2CO_2R^8$ (where $R^8$ is $C_{1-4}$alkyl); $CH_2CONR^6R^7$; or $CH_2CH(OH)$—W—$(CH_2)_2NR^6R^7$ where W is S or NH and $R^6$ and $R^7$ are as previously defined;

$R^2$ represents where m is 0, 1, 2 or 3; $R^9$ represents H or $C_{1-6}$alkyl; $R^{10}$ represents imidazolyl, triazolyl or tetrazolyl, any of which may be optionally substituted by $C_{1-4}$alkyl; and $R^{11}$ represents H, $C_{1-6}$alkyl or halo;

$R^3$ represents $C_{1-6}$alkyl, halo or $NR^6R^7$, where $R^6$ and $R^7$ are as previously defined;

$R^4$ represents $C_{1-7}$alkyl, $C_{3-10}$cycloalkyl optionally substituted by one or more $C_{1-4}$alkyl groups, $C_{3-10}$cycloalkyl$C_{1-4}$alkyl, $C_{6-10}$bicycloalkyl, aryl optionally substituted by one or more substituents selected from ($C_{1-4}$alkyl, $C_{1-4}$alkoxy, hydroxy, halo and trifluoromethyl) $R^4$ is or $NR^{12}R^{13}$ where $R^{12}$ and $R^{13}$ each independently represent H, $C_{1-12}$alkyl, $C_{3-10}$cycloalkyl optionally substituted by one or more $C_{1-4}$alkyl groups, $C_{3-10}$cycloalkyl$C_{1-4}$alkyl, optionally substituted aryl, optionally substituted aryl$C_{1-6}$alkyl or azacyclic or azabicyclic groups, or $R^{12}$ and $R^{13}$ together with the N to which they are attached, form the residue of an optionally substituted azacyclic or azabicyclic ring system which can be represented as (a)

wherein

X represents O, S, $NR^{17}$ or $CH_2$ where $R^{17}$ represents H, $C_{1-4}$alkyl, $CO_2R^a$, $COR^a$, or $SO_2R^a$ where $R^a$ is $C_{1-6}$alkyl, phenyl or benzyl optionally substituted in the phenyl ring by one or more substituents selected from $C_{1-4}$alkyl, $C_{1-4}$alkoxy, halo and trifluoromethyl;

$R^{16}$ is $C_{1-6}$alkyl, $C_{1-6}$alkoxy, hydroxy, oxo, $SC_{1-4}$alkyl, $NR^6R^7$, $NR^9(R^{18}C_{1-4}$alkyl), =$NOR^9$, or where $R^6$, $R^7$ and $R^9$ are as previously defined, $R^{18}$ is halo or trifluoromethyl and y is 2 or 3;

s is 2, 3 or 4;

t is 1, 2, 3, 4, 5, 6, 7 or 8 when X is $CH_2$, or 2, 3, 4, 5, 6, 7 or 8 when X is O, S or $NR^{17}$;

z is 0, 1, 2, 3, 4, 5, 6, 7 or 8; and each $R^{16}$ may be located on any available carbon atom of the azacyclic ring system; or (b) a bridged azabicyclic ring system containing 7–10 ring atoms which is non-aromatic and can contain, in addition to the nitrogen atom to which $R^{12}$ and $R^{13}$ are attached, a second heteroatom selected from O and S, or a group $NR^{17}$, $R^{17}$ being defined above; and $R^5$ represents H or $C_{1-4}$alkyl; and n is 0, 1,2 or 3.

2. A compound as claimed in claim 1 wherein $R^{10}$ represents tetrazolyl optionally substituted by $C_{1-4}$alkyl; $R^3$ represents $C_{1-6}$alkyl or halo; $R^4$ represents $C_{1-7}$alkyl, $C_{3-7}$cycloalkyl, $C_{4-7}$cycloalkylalkyl or aryl optionally substituted by one or more substituents selected from $C_{1-4}$alkyl, $C_{1-4}$alkoxy, hydroxy, halo and trifluoromethyl; m is 0, 1 or 2; and n is 0, 1 or 2.

3. A compound as claimed in claim 2 wherein $R^2$ is

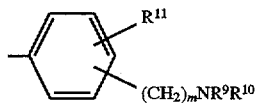

and $R^5$ is H.

4. A compound as claimed in claim 1 wherein $R^1$ represents $C_{1-6}$alkyl, $C_{3-7}$cycloalkyl, cyclopropylmethyl, $CH_2CO_2R^8$ or $CH_2CONR^6R^7$ (where $R^6$, $R^7$ and $R^8$ are as previously defined); $R^2$ is

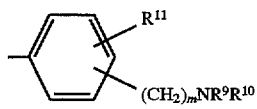

wherein $R^9$, $R^{11}$ and m are as defined for formula (I) and $R^{10}$ represents an imidazolyl group, optionally substituted by $C_{1-4}$alkyl; $R^4$ represents bridged $C_{6-10}$bicycloalkyl or $C_{3-7}$cycloalkyl optionally substituted by one or more $C_{1-4}$alkyl groups; and $R^5$ is H.

5. A compound as claimed in claim 1 wherein $R^{10}$ represents tetrazolyl and m is 0 or 1.

6. A compound as claimed in claim 1 wherein $R^1$ is $C_{1-6}$alkyl; $R^{10}$ is tetrazolyl or imidazolyl; m is 0 or 1; $R^4$ is $C_{3-10}$cycloalkyl, aryl or $NR^{12}R^{13}$; and $R^5$ is H or methyl.

7. A compound as claimed in claim 1 wherein $R^5$ is H.

8. A compound as claimed in claim 1 wherein $R^5$ is methyl.

9. A compound as claimed in claim 1 selected from:

N-[3(R,S)-5-cyclohexyl-2,3-dihydro-1-methyl-2-oxo-1H-1,4-benzodiazepin-3-yl]-N'-[3-((tetrazol-5-yl)aminomethyl) phenyl]urea;

N-[3(R,S)-5-cyclohexyl-2,3-dihydro-1-methyl-2-oxo-1H-1,4-benzodiazepin-3-yl]-N'-[3-((tetrazol-5-yl)amino)phenyl]urea;

N-[3(R,S)-5-cyclohexyl-2,3-dihydro-1-methyl-2-oxo-1H-1,4-benzodiazepin-3-yl]-N'-[3-(N-methyl-N-(tetrazol-5-yl)amino)phenyl]urea;

(+)-N-[3(R)-5-cyclohexyl-2,3-dihydro-1-methyl-2-oxo-1H-1,4-benzodiazepin-3-yl]-N'-[3-(N-methyl-N-(tetrazol-5-yl)amino)phenyl]urea;

(+)-N-[3(R)-5-cyclohexyl-2,3-dihydro-1-methyl-2-oxo-1H-1,4-benzodiazepin-3-yl]-N'-[3-((tetrazol-5-yl)amino)phenyl]urea;

(+)-N-[3(R)-5-cyclohexyl-2,3-dihydro-1-methyl-2-oxo-1H-1,4-benzodiazepin-3-yl]-N'-[3-((tetrazol-5-yl)aminomethyl)phenyl]urea;

(+)-N-[3(R)-2,3-dihydro-1-methyl-2-oxo-5-phenyl-1H-1,4-benzodiazepin-3-yl]-N'-[3-(N-methyl-N-(tetrazol-5-yl)amino)phenyl]urea;

(+)-N-[3(R)-2,3-dihydro-1-methyl-2-oxo-5-phenyl-1H-1,4-benzodiazepin-3-yl]-N'-[3-((tetrazol-5-yl)amino)phenyl]urea;

(+)-N-[3(R)-2,3-dihydro-1-methyl-2-oxo-5-phenyl-1H-1,4-benzodiazepin-3-yl]-N'-[3-((tetrazol-5-yl)aminomethyl)phenyl]urea;

(+)-N-[3(R)-5-cyclohexyl-2,3-dihydro-1-methyl-2-oxo-1H-1,4-benzodiazepin-3-yl]-N'-[4-methyl-3-((tetrazol-5-yl)amino)phenyl]urea;

(+)-N-[3(R)-5-cyclohexyl-2,3-dihydro-1-methyl-2-oxo-1H-1,4-benzodiazepin-3-yl]-N'-[4-methyl-3-(N-methyl-N-(tetrazol-5-yl)amino)phenyl]urea;

(+)-N-[3(R)-2,3-dihydro-1-methyl-2-oxo-5-phenyl-1H-1,4-benzodiazepin-3-yl]-N'-[4-methyl-3-((tetrazol-5-yl)amino)phenyl]urea;

(+)-N-[3(R)-2,3-dihydro-1-methyl-2-oxo-5-phenyl-1H-1,4-benzodiazepin-3-yl]-N'-[4-methyl-3-(N-methyl-N-(tetrazol-5-yl)amino)phenyl]urea;

(+)-N-[3(R)-2,3-dihydro-1-methyl-2-oxo-5-phenyl-1H-1,4-benzodiazepin-3-yl]-N'-[1-(tetrazol-5-yl)indolin-6-yl]urea;

N-[3(R,S)-2,3-dihydro-1,3-dimethyl-2-oxo-5-phenyl-1H-1,4-benzodiazepin-3-yl]-N'-[3-(tetrazol-5-yl)aminomethyl)phenyl]urea;

N-[3(R,S)-1-tert-butyl-2,3-dihydro-2-oxo-5-phenyl-1H-1,4-benzodiazepin-3-yl]-N'-[4-methyl-3-((tetrazol-5-yl)amino)phenyl]urea;

(−)-N-[2,3-dihydro-5-(4-methylpiperazin-1-yl)-2-oxo-1-propyl-1H-1,4-benzodiazepin-3-yl]-N'-[3-(N-methyl-N-(tetrazol-5-yl)amino)phenyl]urea;

N-[3(R,S)-5-cyclohexyl-2,3-dihydro-2-oxo-1-propyl-1H-1,4-benzodiazepin-3-yl]N'-[3-[(1H-imidazol-2-yl)aminomethyl]phenyl]urea;

N-[3(R,S)-5-cycloheptyl-2,3-dihydro-1-methyl-2-oxo-1H-1,4-benzodiazepin-3-yl]N'-[3-[(1H-imidazol-2-yl)aminomethyl]phenyl]urea;

N-[3(R,S)-5-cyclohexyl-2,3-dihydro-2-oxo-1-propyl-1H-1,4-benzodiazepin-3-yl]N'-[3-[(1H-imidazol-2-yl)amino]phenyl]urea;

and pharmaceutically acceptable salts thereof.

10. A method for the treatment of peptic ulcer involving stimulation of CCK and/or gastrin receptors, which method comprising administration to a patient in need thereof a therapeutic amount of a CCK and/or gastrin compound according to claim 1.

11. A pharmaceutical composition comprising a compound as claimed in claim 1 in association with a pharmaceutically acceptable carrier or excipient.

* * * * *